(12) United States Patent
Buckman et al.

(10) Patent No.: US 7,135,010 B2
(45) Date of Patent: *Nov. 14, 2006

(54) METHOD AND APPARATUS FOR RAPID DEPLOYMENT CHEST DRAINAGE

(75) Inventors: Robert F. Buckman, Radnor, PA (US); Jay A. Lenker, Laguna Beach, CA (US); Donald J. Kolehmainen, Laguna Niguel, CA (US)

(73) Assignee: Damage Control Surgical Technologies, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 11/152,413

(22) Filed: Jun. 14, 2005

(65) Prior Publication Data

US 2005/0234390 A1   Oct. 20, 2005

Related U.S. Application Data

(63) Continuation-in-part of application No. 10/676,562, filed on Sep. 30, 2003, now Pat. No. 6,905,484.

(51) Int. Cl.
*A61M 25/00* (2006.01)
(52) U.S. Cl. ............... 604/174; 604/163; 604/604; 604/164.01
(58) Field of Classification Search ............ 604/117, 604/158, 163, 164.01, 164.04, 164.08, 171, 604/174, 179, 180, 506, 511, 513; 128/DIG. 26
See application file for complete search history.

(56) References Cited

U.S. PATENT DOCUMENTS

| | | | |
|---|---|---|---|
| 2,001,638 A | 5/1935 | Gustaf | |
| 3,750,667 A | 8/1973 | Psherichny et al. | |
| 4,767,411 A | 8/1988 | Edmunds | |
| 4,915,694 A | 4/1990 | Yamamoto et al. | |
| 5,215,522 A | 6/1993 | Page et al. | |
| 5,242,398 A | 9/1993 | Knoll et al. | |
| 5,300,045 A | 4/1994 | Plassche, Jr. | |
| 5,336,193 A | 8/1994 | Rom et al. | |
| 5,582,599 A | 12/1996 | Daneshvar | |
| 5,807,341 A | 9/1998 | Heim | |
| 6,447,477 B1 | 9/2002 | Burney et al. | |
| 6,569,121 B1 | 5/2003 | Purow et al. | |

*Primary Examiner*—Sharon Kennedy

(57) ABSTRACT

Devices and methods are disclosed for achieving chest drainage in humans or other animals. Chest drainage is often required following traumatic injury or surgery. The devices and methods disclosed herein are especially useful in the emergency, trauma surgery or military setting. The devices utilize a chest tube with a cutting distal end and a central blunt trocar. The blunt trocar or obturator shields the sharp cutting distal end of the chest tube until controllably retracted. Once the blunt trocar or obturator is retracted, the chest tube is advanced out through its sterile, protective package and into the patient. The blunt trocar is advanced back into its position to shield the sharp tip of the chest tube during patient insertion. The chest tube also includes a hold-down mechanism that is created by an adhesive seal to the patient's chest and ribbons or straps that are wrapped around the chest tube once it is correctly positioned. The straps include adhesive ends to grip the chest tube once the straps are in place.

20 Claims, 11 Drawing Sheets

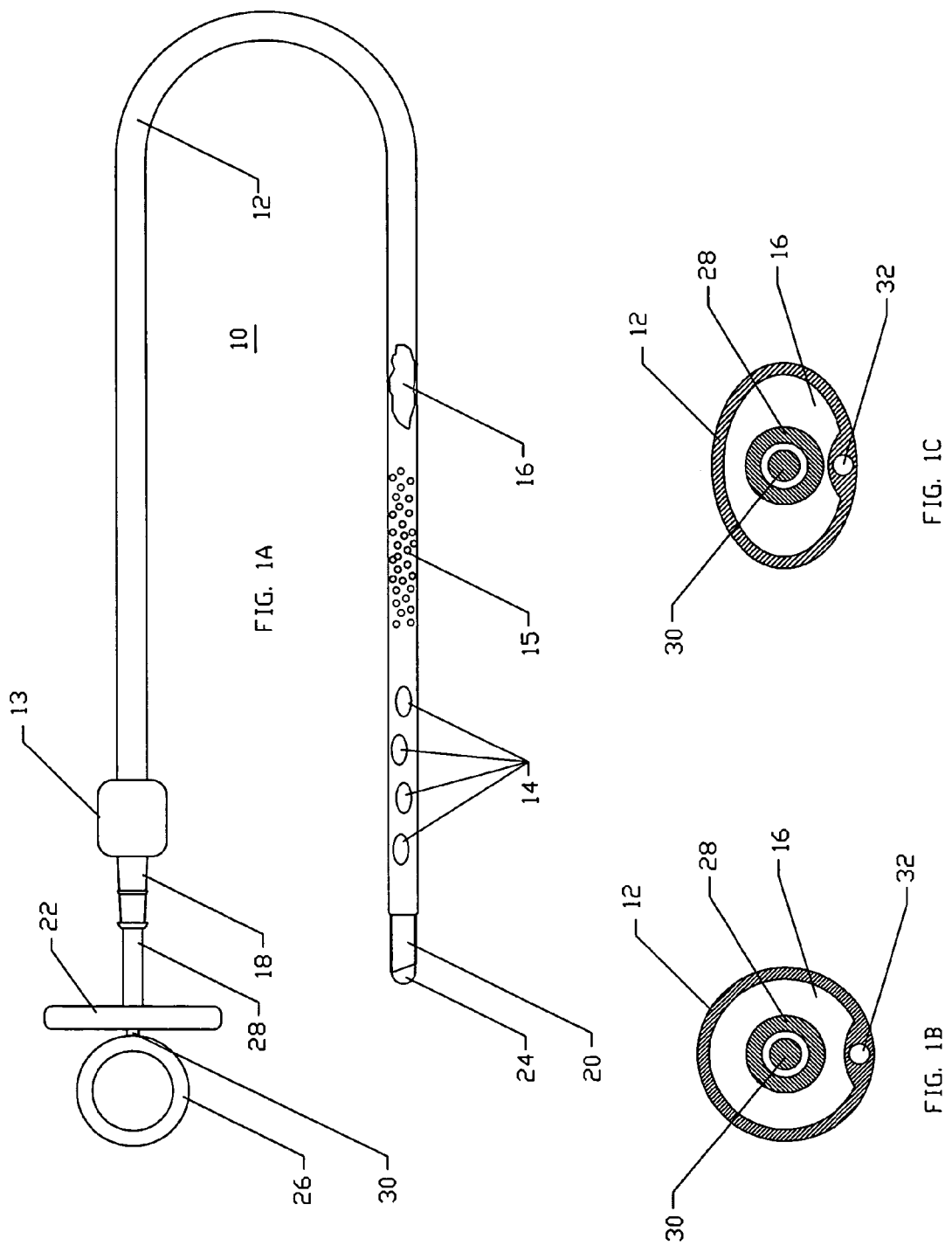

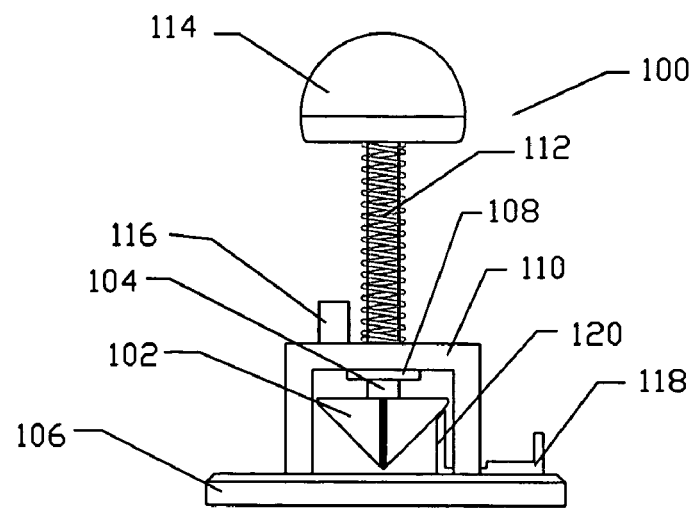
FIG. 6A
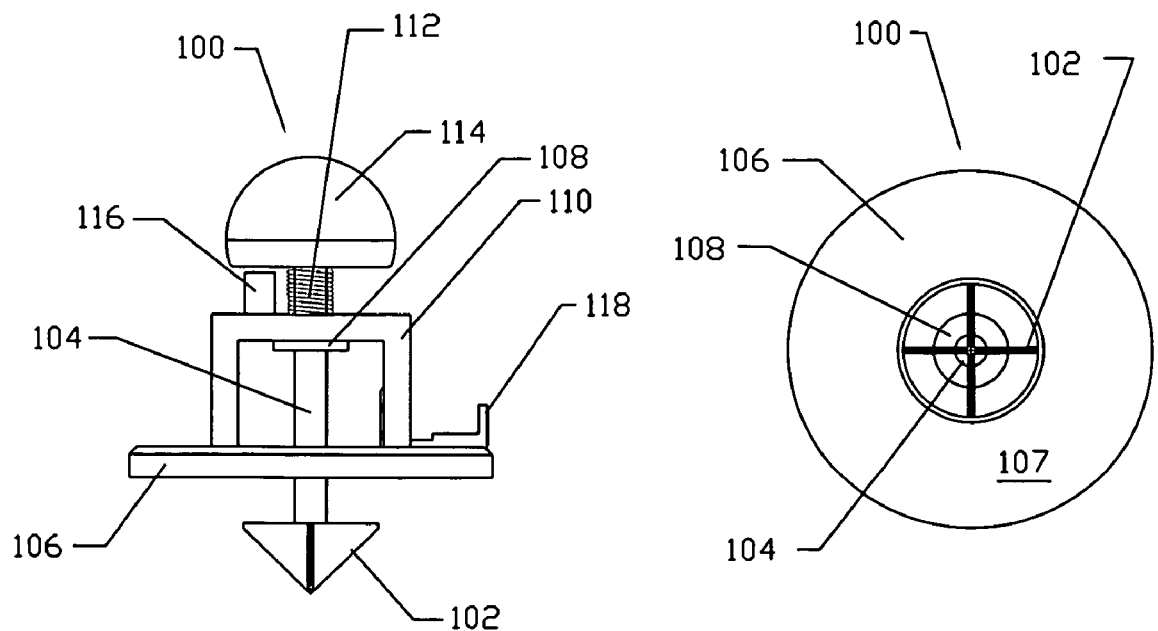
FIG. 6B
FIG. 6C

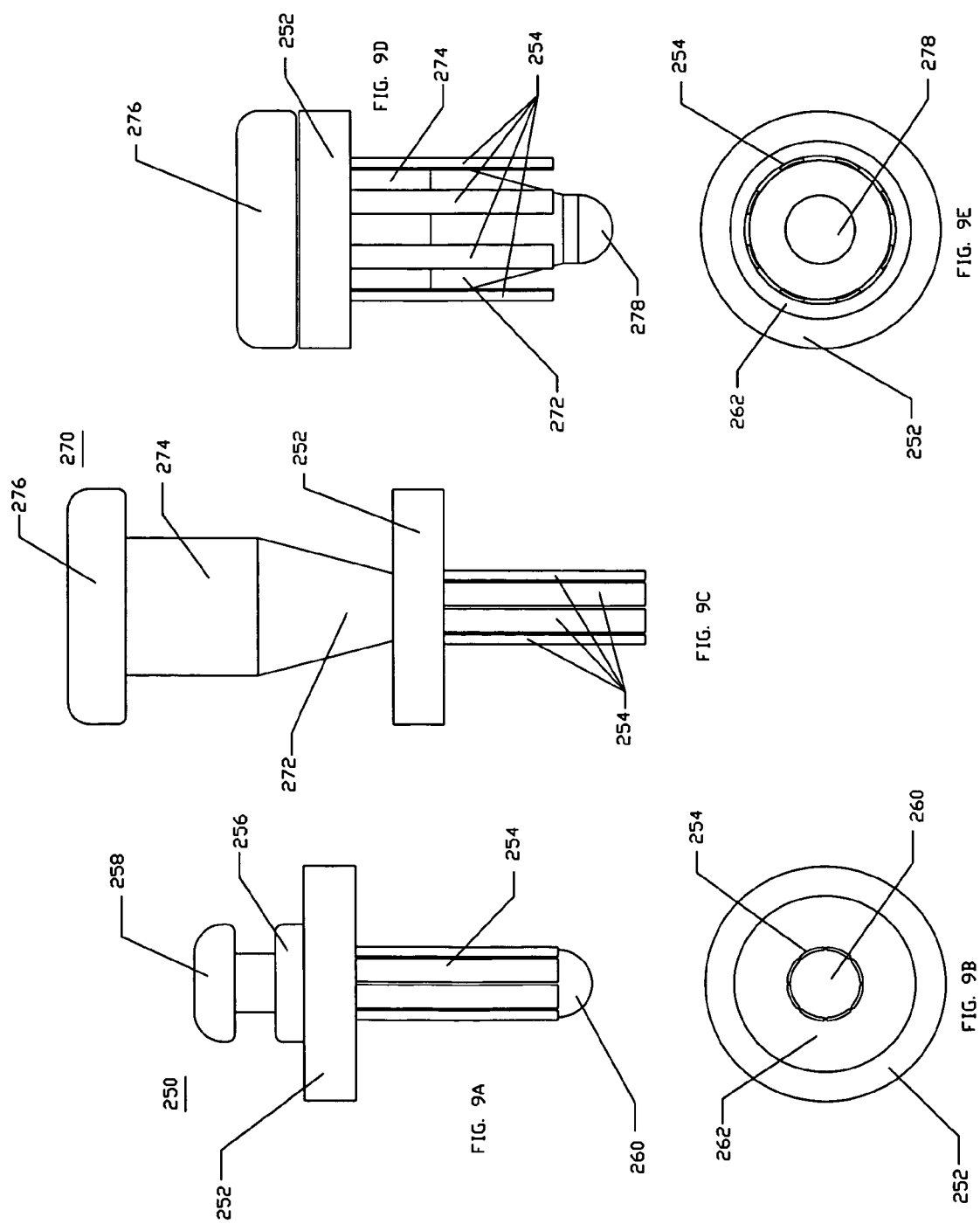

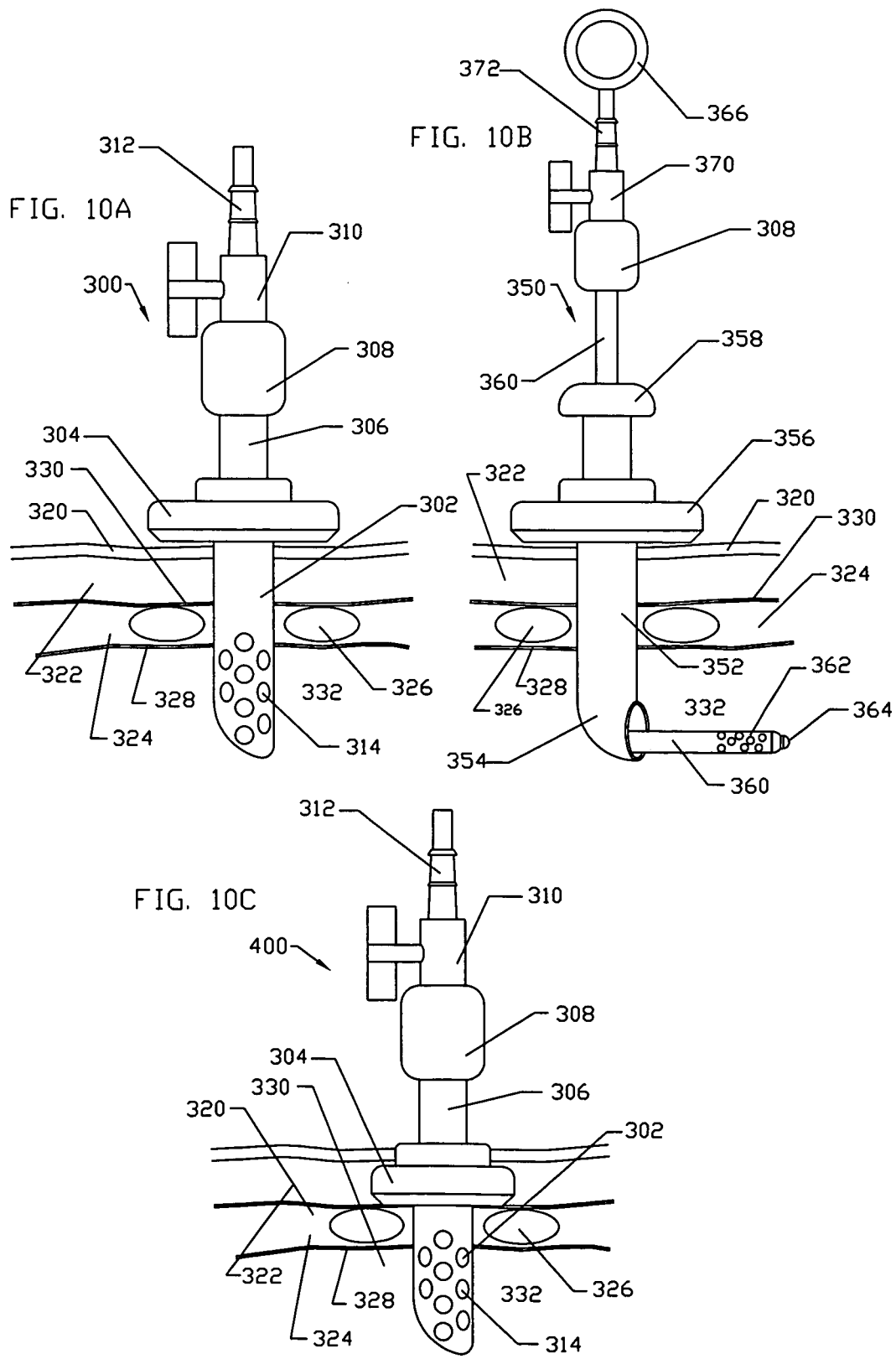

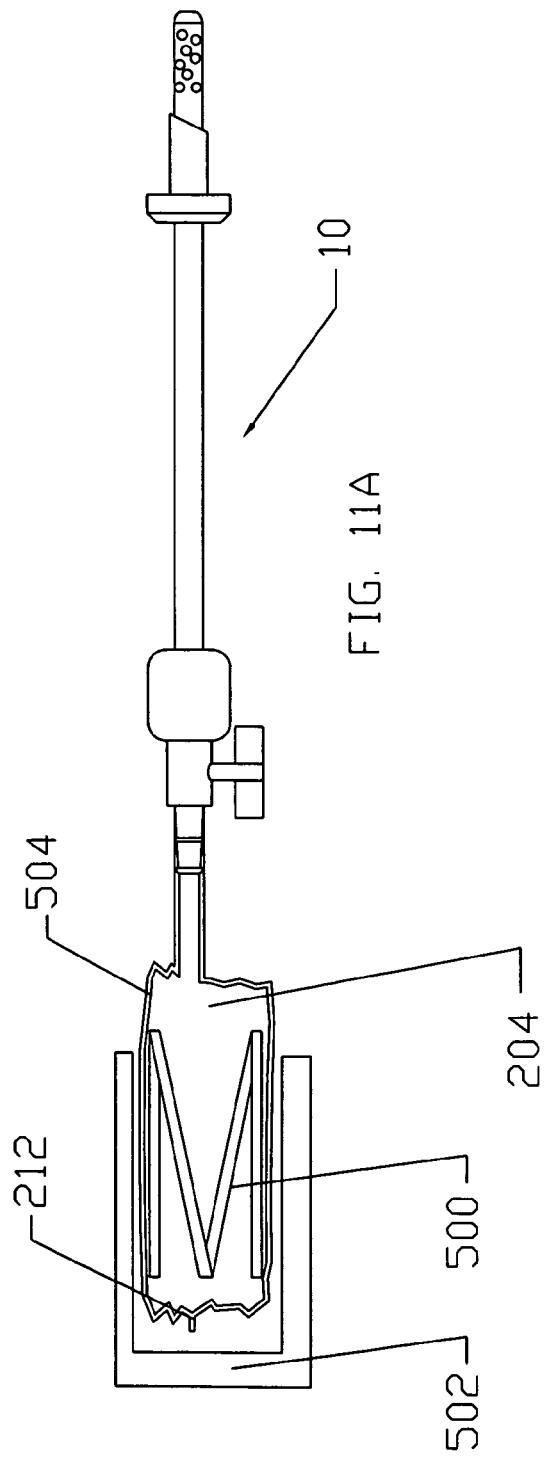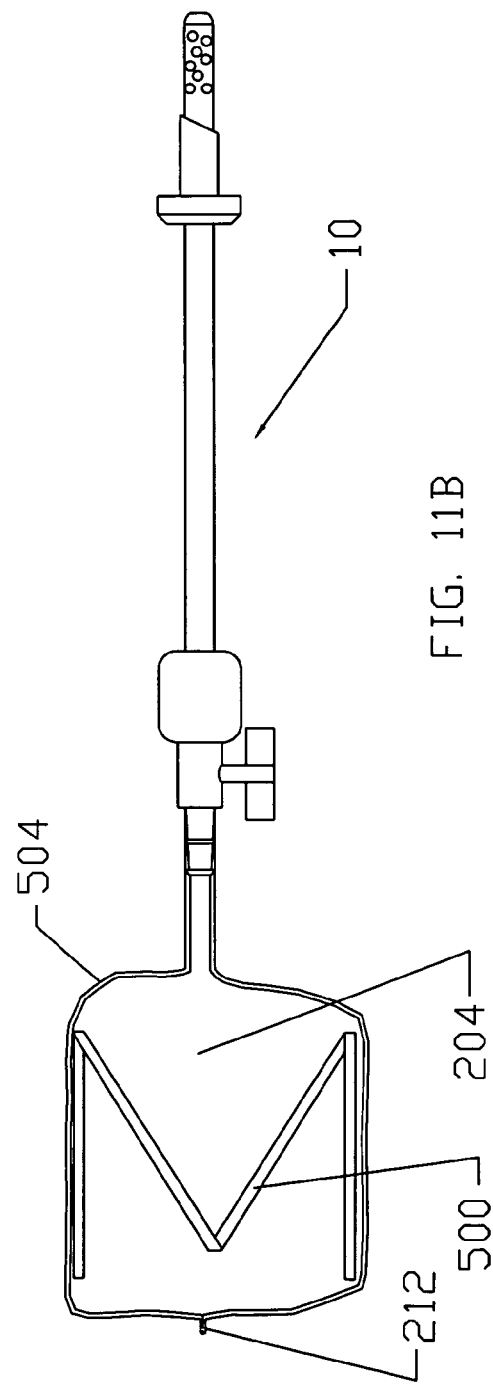

METHOD AND APPARATUS FOR RAPID DEPLOYMENT CHEST DRAINAGE

PRIORITY CLAIM

This application is a continuation-in-part of U.S. patent application Ser. No. 10/676,562 filed Sep. 30, 2003, now U.S. Pat. No. 6,905,484 the entirety of which is hereby included herein by reference.

FIELD OF THE INVENTION

The inventions described below relate to the fields of general surgery, cardiothoracic surgery, trauma surgery, combat medicine, and emergency medical services.

BACKGROUND OF THE INVENTION

Chest drainage tubes are flexible tubes that are placed into a patient's chest cavity to allow for drainage of fluids following trauma or surgery. These chest tubes have one or more holes at the distal end through which the fluid is evacuated from the chest cavity into the lumen of the chest tube. The proximal end of the chest tube includes connectors to allow for passage of the drained fluids from the lumen of the chest tube into a collection device or apparatus. The chest tubes or collection apparatus typically include features to prevent backflow of air into the chest cavity, thus preventing pneumothorax. These backflow prevention features include shutoff valves and duckbill valves. Typical collection apparatus comprises gravity fed drains or vacuum or pump powered drainage mechanisms.

Chest tubes are typically placed into a patient with a stiff trocar mounted to the internal lumen. The trocar is stiff, relatively pointed at the distal end, and allows for advancement of the flexible chest drainage tube into an incision in the chest wall. The stiff, pointed trocar is useful for initial insertion of the chest tube but becomes a dangerous instrument once the chest tube is advanced below the level of the ribs. Use of such internal trocars is not appropriate for non-physician insertion because of the inherent danger of heart or lung perforation.

Maintenance of sterility has always been problematic with chest tubes. Placement of a chest tube, especially in the emergency setting, requires sterile scrub of the incision area and incision into the chest wall with sterile instruments. These incisions are, understandably, difficult to perform aseptically in the field, where the insertion site may be bloody, dirty, or otherwise contaminated. In addition, maintenance of sterility in the area of chest tube penetration into the chest has been difficult as has been the ability to hold the chest tube in position once it has been introduced into the patient. The use of surgical gloves to maintain sterility becomes problematic since the gloves become contaminated quickly in the typical field environment.

New devices and methods are needed to permit rapid placement of chest tubes by less trained individuals in contaminated environments. In addition, improved devices and methods of maintaining sterility at the chest tube wound site and holding the chest tube in place are needed.

SUMMARY OF THE INVENTIONS

The devices and methods described herein provide for placement of chest tubes in contaminated environments using rapid deployment techniques, for maintaining sterility at the penetration site on the patient's chest where the chest tube emerges, and for improved methods of holding the chest tube in place. The present invention is a chest tube that is provided with a double aseptic package that maintains sterility and cleanliness of the chest tube in contaminated environments. Such contaminated environments may occur in the pre-hospital setting or military setting where rain, mud, or other elements exist. The chest tube includes a cannula with a sharpened distal end and a blunt trocar or nose cone that selectively shields or exposes the sharpened distal end.

In another embodiment, a region on the chest tube is configured to allow for maximum friction while gripping the chest tube through the package material. In another embodiment, a region on the packaging is fabricated from gripping material to facilitate pushing the chest tube inside the packaging. The region on the packaging optimized for gripping the chest tube is optionally fabricated from elastomeric material to facilitate moving the chest tube inside and relative to the inelastic package. In another embodiment, the blunt trocar, itself, is shaped so as to penetrate the package without the need of a separate sharp tip. This blunt trocar is also suitable for blunt dissection into the chest wall once the initial incision has been completed.

The blunt trocar can be manually retracted within the cannula exposing the sharpened distal tip of the cannula. The cannula is punched through the inner layer of package by way of the sharp tip and the blunt trocar is now replaced to its protective position. The chest tube is now advanced into the prepared incision in the chest cavity.

The chest tube may further include a malleable region along part or all of its length to facilitate bending of the chest tube into a pre-determined shape. The use of a curved or bent shape on the part of the chest tube facilitates placement beneath the ribs but above the lungs and heart.

Another feature of the invention is a patch, disc, plate, or membrane of adhesive-faced impermeable material that is adhered to the site where the wound will be created in the chest wall. The patch may also be coated with materials that have disinfectant properties. The patch also includes straps disposed, for example, in a starburst pattern. Once the site has been swabbed with disinfectant, the disc of material is adhesively placed on the skin at the site of the incision. The incision is now made through the patch of material. This patch serves as a sterile barrier following placement of the chest tube. The straps serve to hold onto the chest tube to maintain its position once placed. The straps are wrapped around the chest tube and adhesively affixed to the shaft of the chest tube after placement, thus securely holding the chest tube to the disc, which is affixed to the chest wall of the patient. The patch is optionally pre-mounted to the chest tube inside the package. In this embodiment, the chest incision is performed prior to attachment of the patch to the patient. In another embodiment, the disc is integral to the inner packaging material so that once the outer packaging material is removed, the patch may be immediately placed against the chest over the region of the incision.

In another embodiment of the invention, a chest tube is designed with an integral tip that permits the chest tube to be advanced out of the package by forcing a fenestration in the package wall or seal. The integral tip may be a cutting member that is selectively exposed by the operator and then re-protected following package penetration. This same cutting member may also be used to make the initial incision in the chest wall of the patient. The member that re-protects the cutting edge may be a blunt nose that is suitable for bluntly dissecting the tissue between the ribs. In another embodiment of the invention, the blunt nose is configured to form a wedge so that it is able, itself, to force a fenestration in the package or package seal, thus obviating the cutting edge.

The chest tube package can be configured with a region that allows for manipulation of the contents so that said contents, the chest tube, may be advanced out of the package by manual application of force. The region permitting manipulation is an elastic area that is deformable relative to the rest of the package or it is a movable region with a sliding seal between itself and the rest of the package. Either method maintains sterility within the package during moving of the contents. The inner package containing the chest tube can also comprise a region that is specially designed to facilitate penetration by the chest tube. This penetration region is a weakened part of the heat seal or a specially designed port that opens only to permit the chest tube to penetrate the inner package.

To facilitate placement of the chest tube, a specialized cutter is configured to perform the initial incision into the chest wall without penetrating below the level of the ribs. This specialized cutter comprises safety features to prevent premature deployment and to prevent cutting too deeply into the chest. This cutter is actuated by manual, electrical or hydraulic/pneumatic force. It may be configured to be a positive displacement cutter or it may be a punch that is loaded and fired or activated under pre-determined force.

The chest tube comprises a short insertion portion (the distal segment intended and adapted for insertion into the body of the patient) and a stop to prevent it from being inserted too far into the patient. The short insertion portion has a blunt distal end and is capable of being inserted into a fenestration or incision in the chest wall that was created by either a scalpel and blunt dissection as would be performed by a gloved finger, a Kelly clamp, or a specialized trocar and obturator. The short chest tube is inserted through the incision into the chest cavity. The short chest tube projects through the skin, fat, fascia, between the ribs, and finally through the pleural lining. The tip of the chest tube is soft or blunt or both, and contains no edges or roughness that might erode underlying tissues. The short chest tube is terminated on its proximal segment (proximal to the stop) with a manually openable and closeable valve or it is terminated with a one-way valve that permits only removal of fluids and air from the chest cavity. The short chest tube comprises a flange that prevents excessive penetration into the chest cavity. The flange is designed to stop at the level of the skin surface, or, in another embodiment, the flange is smaller and is inserted into the incision but does not penetrate below the level of the top of the ribs.

In yet another embodiment, should lateral penetration of the chest tube be desirable, the short chest tube comprises a trocar and obturator that bluntly penetrates the incision to a pre-determined depth such that it is depth-limited. The trocar further comprises a right angle turn at its distal end that serves to deflect a secondary longer chest tube that is placed through the trocar and which extends laterally in the pleural space to the desired location. The trocar and secondary chest tube comprise a seal system to prevent gas passage between the two components. The trocar further comprises an angular orientation marker that provides an indication to the operator of the direction where the secondary chest tube will be deflected. The orientation markers may be aligned by the practitioner to point to the head or the feet (or other anatomical landmark) so that the deflection is always in a pre-determined direction.

The short chest tube can be installed on a patient by unskilled, or relatively unskilled, medical personnel to treat a trauma pneumothorax in the field. It cannot be placed unsafely and thus paramedics or Emergency Medical Technicians (EMTs) may install, or place, the chest tube into patients while they are in the field or the emergency department. The short chest tube is preferably coupled with a specialized blunt or automatic tissue dissector that safely dissects an incision through the ribs. The short chest tube as well as other chest tubes disclosed herein are suitable for treatment of patients experiencing a sucking chest wound or other trauma pneumothorax.

In another embodiment of the chest tube, the cross-sectional configuration of the chest tube is non-circular. The chest tube preferably comprises an elliptical cross-section that permits a large internal flow channel to be passed between ribs with a narrow space therebetween.

In another embodiment of the chest tube, the central or through lumen of the chest tube and the fenestrations or openings at the distal tip are coated with anti-thrombogenic agents such as but not limited to heparin. Heparin may be covalently or ionically bonded to the polymeric material of the chest tube. The exterior and interior surfaces of the chest tube are optionally also coated with antibiotic materials to minimize the risk of infection.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein. These and other objects and advantages of the present invention will be more apparent from the following description taken in conjunction with the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIG. 1A illustrates a side view of a chest tube;

FIG. 1B illustrates a lateral cross-section of the central area of the chest tube comprising a generally circular cross-sectional profile;

FIG. 1C illustrates a lateral cross-section of the central area of the chest tube comprising a generally elliptical cross-sectional profile;

FIG. 6A illustrates a side view of a chest wall punch, with a retracted blade;

FIG. 6B illustrates a side view of a chest wall punch with the blade advanced;

FIG. 6C illustrates a bottom view of a chest wall punch with the blade advanced;

FIG. 9A illustrates a side view of an expandable sheath and blunt obturator;

FIG. 9B illustrates a bottom view of the expandable sheath and blunt obturator;

FIG. 9C illustrates a side view of the expandable sheath with the blunt obturator removed and a tapered expanding obturator just being inserted;

FIG. 9D illustrates a side view of the expandable sheath with the tapered expanding obturator fully inserted so that the collet-like split sheath sides are fully expanded;

FIG. 9E illustrates a bottom view of the expandable sheath with the tapered expanding obturator fully inserted;

FIG. 10A illustrates a side view of a short chest tube, shown placed through a cross-sectional view of the outer chest wall wherein a limit flange stops at the level of the skin;

FIG. 10B illustrates a side view of a short deflecting trocar and chest tube placed into a thorax or chest wall of a patient;

FIG. 10C illustrates a side view of a short chest tube placed into a thorax or chest wall of a patient wherein a limit flange stops at the level of the ribs;

FIG. 11A illustrates a side view of the chest tube package of FIG. 8B further comprising an internal vacuum pump in its collapsed state; and FIG. 11B illustrates a side view of the chest tube package of FIG. 11A in its expanded, vacuum-generating state.

DETAILED DESCRIPTION OF THE INVENTION

Figure 2A:
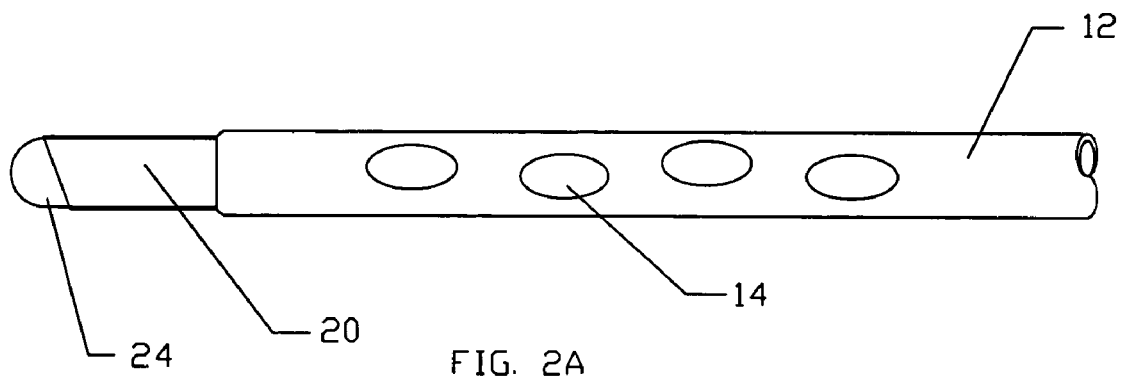
FIG. 2A illustrates a side view of the distal tip of the chest tube with a blunt trocar or obturator in the advanced configuration so that the sharp cutter edge is protected.

In accordance with one or more embodiments of the present invention, a chest tube, packaging and accessory components are described herein. In order to fully specify this preferred design, various embodiment specific details are set forth, such as the number and makeup of the hold-down straps, cutter action and packaging materials. It should be understood, however that these details are provided only to illustrate the presented embodiments, and are not intended to limit the scope of the present invention.

The invention, which is generally termed a catheter or cannula, can be described as being an axially elongate hollow tubular structure having a proximal end and a distal end. The axially elongate structure further has a longitudinal axis and has an internal through lumen that extends from the proximal end to the distal end for the passage of instruments, fluids, tissue, or other materials. The axially elongate hollow tubular structure is generally flexible and capable of bending, to a greater or lesser degree, through one or more arcs in one or more directions perpendicular to the main longitudinal axis. As is commonly used in the art of medical devices, the proximal end of the device is that end that is closest to the user, typically an EMT, paramedic, surgeon, or emergency physician. The distal end of the device is that end closest to the patient or that is first inserted into the patient. A direction being described as being proximal to a certain landmark will be closer to the user, along the longitudinal axis, and further from the patient than the specified landmark. The diameter of a catheter is often measured in "French Size" which can be defined as 3 times the diameter in millimeters (mm). For example, a 15 French catheter is 5 mm in diameter. The French size is designed to approximate the circumference of the catheter in mm and is often useful for catheters that have non-circular cross-sectional configurations.

FIG. 1A illustrates a side view of a chest tube 10 of the present invention. The chest tube 10 comprises a length of cannula tubing 12, an optional integral valve 13, a plurality of drainage ports 14, an optional region of gripping surface 15 on the cannula tubing 12, a drainage lumen 16, a drainage connector 18, a cutter 20, a cutter handle 22, an obturator 24, an obturator handle 26, a cutter control mechanism 28, an obturator control rod 30 (see FIGS. 1B and 1C), and a malleable shaft 32.

The cannula tubing 12 is an axially elongate hollow tube affixed at the proximal end to a drainage connector 18. The central or through lumen of the drainage connector 18 is in communication with the central of through lumen 16 of the chest tube 10. The drainage ports 14 are penetrations communicating from the outside of the cannula tubing 12 and are in communication with the inner lumen 16. The cutter 20 is affixed to the distal end of the cutter control mechanism 28. The cutter control mechanism 28 is slideably affixed within the central or drainage lumen 16 of the cannula tubing 12. The cutter handle 22 is affixed to the proximal end of the cutter control mechanism 28. The obturator 24 is affixed to the distal end of the obturator control rod 30, which is slideably mounted within the drainage lumen 16 of the cannula tubing 12. The obturator handle 26 is affixed to the proximal end of the obturator control rod 30. The malleable shaft 32 is affixed to, or integral to, the cannula tubing 12 and runs along at least a portion of the length of the cannula tubing 12. The obturator control rod 30 and the cutter control mechanism 28 both traverse the cannula tubing 12 from approximately its proximal end to approximately its distal end. The valve 13 is optional and is optionally configured integrally to the cannula tubing 12 or removably affixed to the drainage connector 18. The gripping surface 15 is integral to the cannula tubing 12 or it is optionally a separate structure that is movably able to grip the cannula tubing 12.

Further referring to FIG. 1A, the chest tube 10 is designed to be placed within a patient's chest and into the patient's chest through an incision in the patient's chest to provide for drainage. Using additional components such as a stopcock or one-way valve 13, the chest tube prevents backflow of air or contaminants back into the chest. Such backflow of air or contaminants could lead to a pneumothorax or infection.

The valve 13 comprises a closeable central orifice that is also openable permitting the obturator control rod 30, the cutter control mechanism 28, the cutter 20 and the obturator 24 to pass therethrough. The valve 13 is either a one-way valve permitting flow only from the distal tip of the chest tube 10 and not retrograde back toward the distal tip of the chest tube 10 (a duckbill valve, for example) or a stopcock type valve (a ball valve) that is manually moved or moved by another type of power source such as a solenoid or motor. The valve 13 may be integral to the chest tube 10 or a separate component added proximal to the drainage connector 18.

The gripping surface 15 may be a region of roughness on the surface of the cannula tubing 12. This roughness may be created by a series of protrusions or depressions in the surface of the cannula tubing 12 or any other texturing or knurling. The gripping surface 15 may also be a separate structure that is slidably, concentrically affixed to the cannula tubing. When the gripping surface 15 is withdrawn proximally, it slides relative to the cannula tubing 12. When the gripping surface 15 is advanced distally, it grips the cannula tubing 12 in the same manner as a jamb cleat or ratchet and advances the cannula tubing 12 distally.

The materials used in the manufacture of the cannula tubing 12 of the chest tube 10 include but are not limited to polyvinyl chloride, PEBAX, polyurethane, polyester, polyethylene, PEEK, polypropylene, polytetrafluoroethylene, polyetheretherketone, fluorinated ethylene propylene, polytetrafluoroethylene-perfluoromethylvinylether and silicone rubber. In order to minimize the risk of kinking, the wall of the cannula tubing 12 may be extruded with integral spiral or braided reinforcements manufactured from materials such as but not limited to stainless steel wire, polyimide strands and the like. The cannula tubing 12 may be manufactured from materials with variable durometer or hardness. For example, the proximal end of the cannula tubing may be of harder durometer or thicker wall construction to make that area stiffer than the distal end, thus enhancing pushability and column strength of the chest tube 10.

The obturator control rod 30 and the cutter control mechanism 28 possess column strength and are substantially inelastic in tension. The obturator control rod 30 and the cutter control mechanism 28 are, however flexible to at least some degree and allow bending of the chest tube 10 to minimize the risk of perforating internal organs on the patient while the chest tube 10 is being inserted. The obturator control rod 30 and the cutter control mechanism 28 are fabricated from materials such as, but not limited to, stainless steel, nitinol, Elgiloy and the like. The structures of the obturator control rod 30 and the cutter control mechanism 28 are a solid or tubular axially elongate metal or, preferably, a coil or double helix or a braided reinforcement with a polymer coating or coextrusion. Such polymer coatings include, but are not limited to, Pebax, PVC, PEEK, PTFE, PET, PETG, polyethylene, polypropylene and the like. In another embodiment, the obturator control rod 30 can extend substantially the entire length of the chest tube 10 or it can be disposed only near the distal end of the chest tube 10. The obturator control rod 30 can be spring loaded and triggered to automatically advance once the cutter 20 has passed beneath the ribs and into the chest cavity. The trigger for the obturator control rod 30 can be pressure loaded so that unloading the pressure from the obturator 24, which is initially behind the cutter 20 allowing the cutter 20 to penetrate tissue, causes the blunted or rounded obturator 24 to advance distally and blunt the cutter 20.

The interior walls of the tube 12, which form the exterior of the drainage lumen 16 and the distal ports are optionally coated with antithrombogenic materials to minimize the risk of thrombus. The antithrombogenic materials include but are not limited to heparin. The antithrombogenic materials are mechanically, covalently or ionically bonded to the material of the tube 12. The valve 13 is optionally also coated with similar antithrombogenic agents as well as is the inner lumen of the drainage connector 18. The exterior of the tube 12 as well as the interior surfaces of the chest tube 10 are optionally coated with antibiotics to minimize the risk of infection. This is especially important in contaminated environments. Such antibiotics include but are not limited to erythromycin, amoxicillin, sulfa drugs and the like.

The diameter of the cannula tubing 12 ranges from 1 mm to 30 mm and preferably between 2 mm and 15 mm. The length of the cannula tubing 12 ranges between 10 cm and 200 cm and most preferably ranges between 30 cm and 100 cm.

The malleable shaft 32 is preferably a length of stainless steel or other metal, in the form of wire or strand, for example, that is embedded within the wall of the cannula tubing 12. This malleable shaft may or may not be removable from the chest tube 10. The malleable shaft 32 extends along at least a portion of the cannula tubing 12 but preferably extends along the full length of the cannula tubing 12. The malleable shaft 32 is sized so that it may be bent by manual force but resists bending by resilient or elastic forces imposed thereon by the cannula tubing 12.

The drainage connector 18 is preferably fabricated from materials such as but not limited to polycarbonate, polyvinyl chloride, polyethylene, polypropylene and the like. The drainage connector 18 is preferably insert molded or affixed using adhesives to the cannula tubing 12. The drainage connector 18 preferably comprises a single through lumen. The drainage connector 18 may, however, be "Y" shaped or trident shaped and have multiple connections. Such connections typically use hose barb type fittings but may also have Luer type fittings or other bayonet or threaded connections for interface with other equipment. The drainage connector 18 is sized so that the cutter control mechanism 28 and the obturator control rod 30 may be slideably passed therethrough. The drainage connector 18, preferably is sized so that the cutter 20 and obturator 24 may be completely removed from the chest tube 10.

The cutter 20 is preferably a circular cutter with its edge beveled to the outside. A circular cutter is also known as a trephine. The plane of the front edge of the circular cutter 20 is preferably not orthogonal to the axis of the tube 12 of the chest tube 10. The plane of the front edge of the circular cutter 20 is, preferably, disposed at an angle between 5 degrees and 60 degrees from the plane that is orthogonal to the axis of the chest tube 10.

FIG. 1B illustrates a lateral cross-section of the central area of the chest tube 10 with the cannula tubing 12 cross section showing the malleable shaft 32 as an integral part of the tubing. The drainage lumen 16 of cannula tubing 12 has the cutter control mechanism 28 and obturator control rod 30 running co-axially throughout the length of said lumen 16. The cross-sectional outer profile of the cannula tubing 12 is generally circular.

FIG. 1C illustrates a lateral cross-section of the central area of another embodiment of the chest tube 10 with the cannula tubing 12 cross-section showing the malleable shaft 32 as an integral part of the tubing. The drainage lumen 16 of the cannula tubing 12 further comprises the cutter control mechanism 28 and the obturator control rod 30 running coaxially throughout the length of said lumen 16. The outer profile of the cannula tubing 12 is generally elliptical. An elliptical or rounded rectangular cross-sectional configuration enhances placement of the chest-tube through the intercostal space. By aligning the major axis of the ellipse with the direction of the rib disposition and the minor axis transverse to the direction of the ribs, a chest tube of larger drainage capacity than would normally be allowed by the rib spacing may be inserted between the ribs. Clamps and other devices can be used to insert a large round chest tube that would not normally fit between the ribs except by compressing, or pre-flattening, the tubing cross-section prior to insertion. This compression technique is tedious, wastes time, requires sterile equipment and technique, and increases the chance of contamination to the patient.

FIG. 2A illustrates a side view of the distal end of the cannula tubing 12 comprising the cutter 20 and obturator 24, further comprising the plurality of drainage ports 14. The cutter 20 and obturator 24 are in the extended or protected position.

Referring to FIGS. 2A and 1A, the cutter 20 is blunted or protected by the extended obturator 24 so that the sharp edge or sharp tip of the cutter 20 cannot inadvertently cut through the sterile packaging of the chest tube 10. Such blunting or protection of the cutter 20 by the obturator or blunt tip 24 is selective or controllable. The cutter control mechanism and obturator control rod thus provide means for longitudinally translating the cutter relative to the obturator 24, so that it may be selectively extended to put the cutting edge distal of the obturator 24. The means for longitudinally translating the cutter 20 may also be implemented such that the obturator 24 is longitudinally fixed relative to the cannula tubing, in addition to the longitudinally slidable obturator 24 illustrated in FIGS. 2A, 2B and 2C.

Figure 2B:
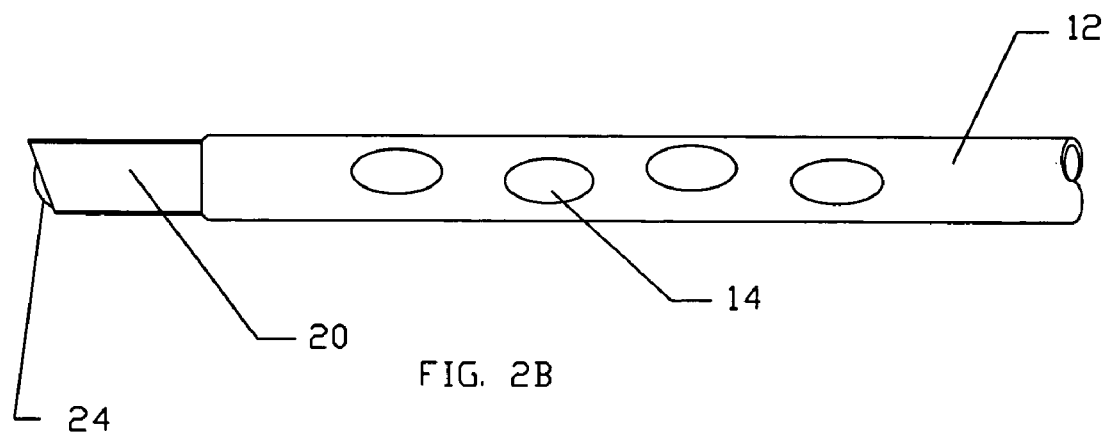
FIG. 2B illustrates a side view of the tip of the chest tube with the blunt trocar or obturator in the retracted configuration so that the sharp edge of the cutter is exposed.

FIG. 2B illustrates a side view of the distal end of the cannula tubing 12 comprising the cutter 20 and obturator 24, further comprising the plurality of drainage ports 14. The cutter 20 is in the extended position while the obturator 24 slightly retracted.

Referring to FIG. 2B, the obturator 22 is slightly retracted to expose the sharp edge of the cutter 20. The sharp edge of the cutter 20 is now useable to punch through the packaging of the chest tube to facilitate using the tube in emergency conditions or contaminated environments.

Figure 2C:
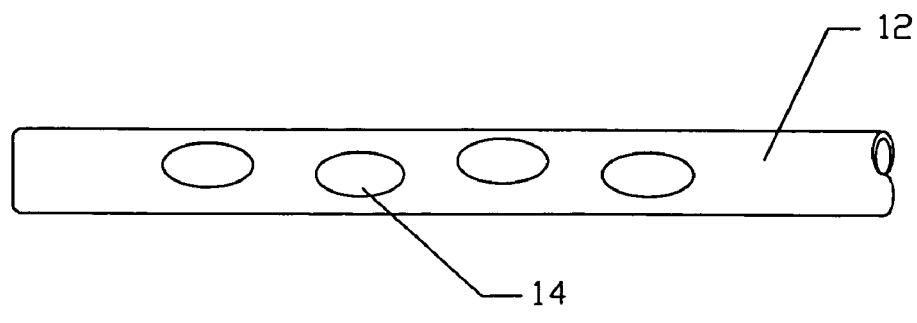
FIG. 2C illustrates a side view of the tip of the chest tube with the blunt trocar or obturator and the cutting blade retracted and removed back through the proximal end of the chest tube.

FIG. 2C illustrates a side view of the distal end of the cannula tubing 12 comprising the plurality of drainage ports 14. Referring to FIGS. 1A and 2C, the cutter 20 and obturator 24 are not visible in this view, as they have been removed from the cannula tubing 12 to open the drainage lumen 16 in order to perform the designed function of the chest tube 10.

Figure 3A:
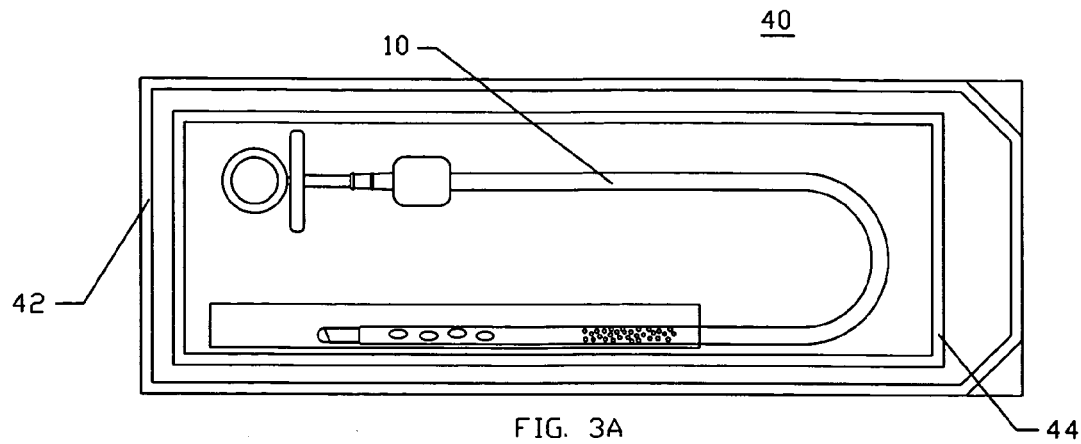
FIG. 3A illustrates a double aseptic package around the chest tube.

FIG. 3A illustrates the packaging 40 of the present invention. The packaging 40 contains the chest tube 10, and comprises an outer package 42 and an inner package 44. The outer package 42 and inner package 44 are sterile barriers for the chest tube 10. The inner package 44 and the outer package 42 are, preferably, polyethylene pouches that are closed using heat seals. The heat seals are typically from ⅛ inch to ½ inch wide around the perimeter of the pouches. The pouches may have regions fabricated from sterile barrier such as Tyvek®, or other material, that is suitable for use with ethylene oxide (ETO) sterilization and allows said ETO to pass into the pouch but prevents contamination from entering the pouch. The weakened area of the seal can be an area where the seal is less wide (⅛ to 1/16 inch) than the rest of the seal.

In another embodiment, the outer package 42 is a tray fabricated from materials such as, but not limited to, polystyrene, polyvinyl chloride, PETG and the like. The trays are typically thermoformed and are covered with a lid fabricated from Tyvek, PETG, polyethylene or the like. The lid is preferably heat sealed to a flange at the open end of the tray. A tray is advantageous over a pouch in that it offers protection against crushing that is not provided by the pouch and can include integrally molded standoffs and restraints to hold the product in place during shipping. The tray, however, is larger, heavier, and more difficult to store and dispose.

The double sterile barrier is intended to give the practitioner the option of not using the device after initial assessment of the patient and also for cleanliness and sterility purposes in the field.

Figure 3B:
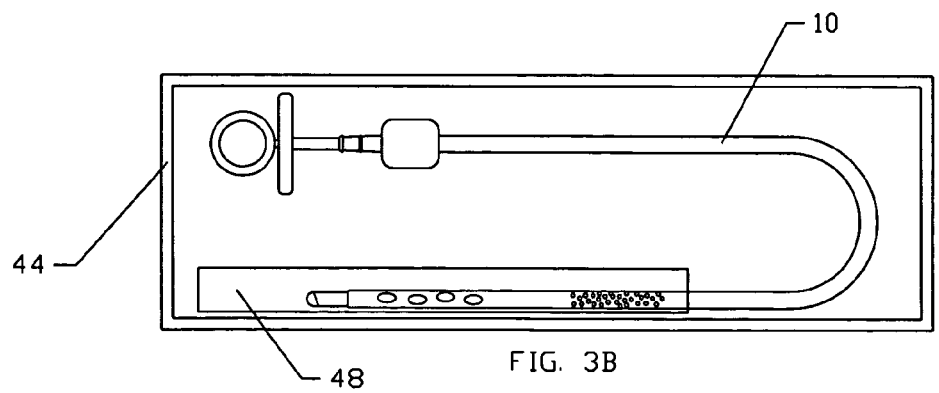
FIG. 3B illustrates the aseptic package with the outer layer removed.

FIG. 3B illustrates the packaging 40 with the outer package 42 removed. The inner package 44, further comprising a gripping region 48, is still sealed and protects the chest tube 10 from contamination. The gripping region 48 provides an area on the package where the operator may more easily grab the chest tube 10 without slipping. This gripping region 48 is a high friction region relative to the rest of the package. The gripping region 48 is, in a further embodiment, elastomeric in structure and allows the operator to advance the chest tube 10 while the flexible or inflexible, but inelastic, inner package 44 remains relatively undistorted and stable. Suitable materials for fabricating the gripping region 48 include, but are not limited to, polyurethane, silicone rubber, thermoplastic elastomers such as C-Flex, and latex rubber.

In yet another embodiment, the gripping region 48 is movably attached to the inner package 44 by means of a sliding or moving seal. This sliding or moving seal is a gasket between the gripping region 48 and the inner package 44 that prohibits passage of contaminants into the inner package 44 but still permits translation or movement of the gripping region 48 relative to the inner package 44. In one exemplary embodiment, the gripping region 48 is a plunger that impinges on the friction surface 15 on the chest tube 10. The operator depresses the plunger or gripping region 48 and the chest tube 10 is forced against and through the inner package 44 seal at seal penetration point 46.

Figure 3C:
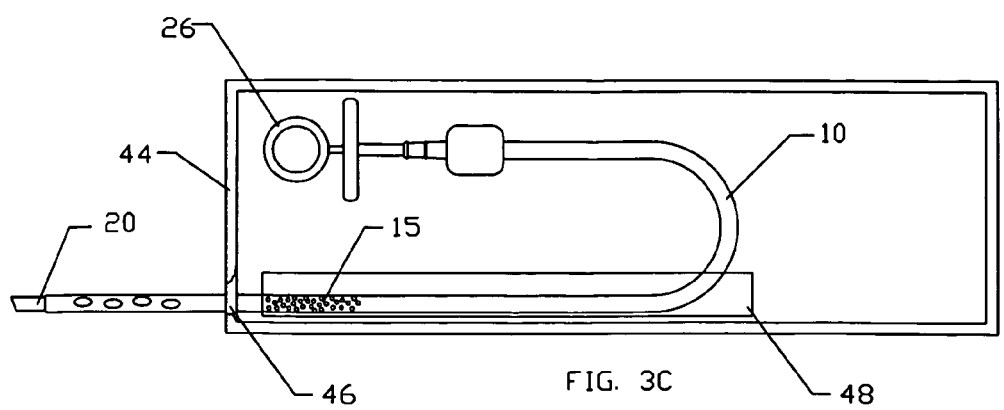
FIG. 3C illustrates the aseptic package with the chest tube advanced out through the inner layer of the package.

FIG. 3C illustrates the packaging 40 of the chest tube 10 in the inner package 44, further comprising the gripping region 48, with the obturator handle 26 in the partially retracted position. The chest tube 10 in this configuration will allow inner package seal penetration 46 to occur as a result of advancement of the chest tube 10 with the cutter 20 exposed, thus penetrating the inner package 44 seal. The obturator 24 is not visible in this view as it is retracted into the cutter 20 and cannula tubing 12. This allows for cutter 20 penetration through the inner package 44 at the seal penetration point 46 to maintain sterility until advancement and deployment into the patient.

In another embodiment of the invention, the inner package 44 seal is weakened at a specific area where the chest tube is intended to penetrate the seal. This weakened area is, preferably, visibly marked to ensure that the chest tube penetrates the seal at the weakened area of the inner package 44. In yet another embodiment, an openable window is provided in the inner package 44 where the chest tube 10 is to be advanced out of said inner package 44. This openable window is, for example, a normally closed elastomeric valve (a duckbill or other slit membrane, for example) that is pried open by the chest tube obturator or its cutter. An optional thin seal layer is used to maintain sterility over the openable window, prior to opening.

Figure 4:
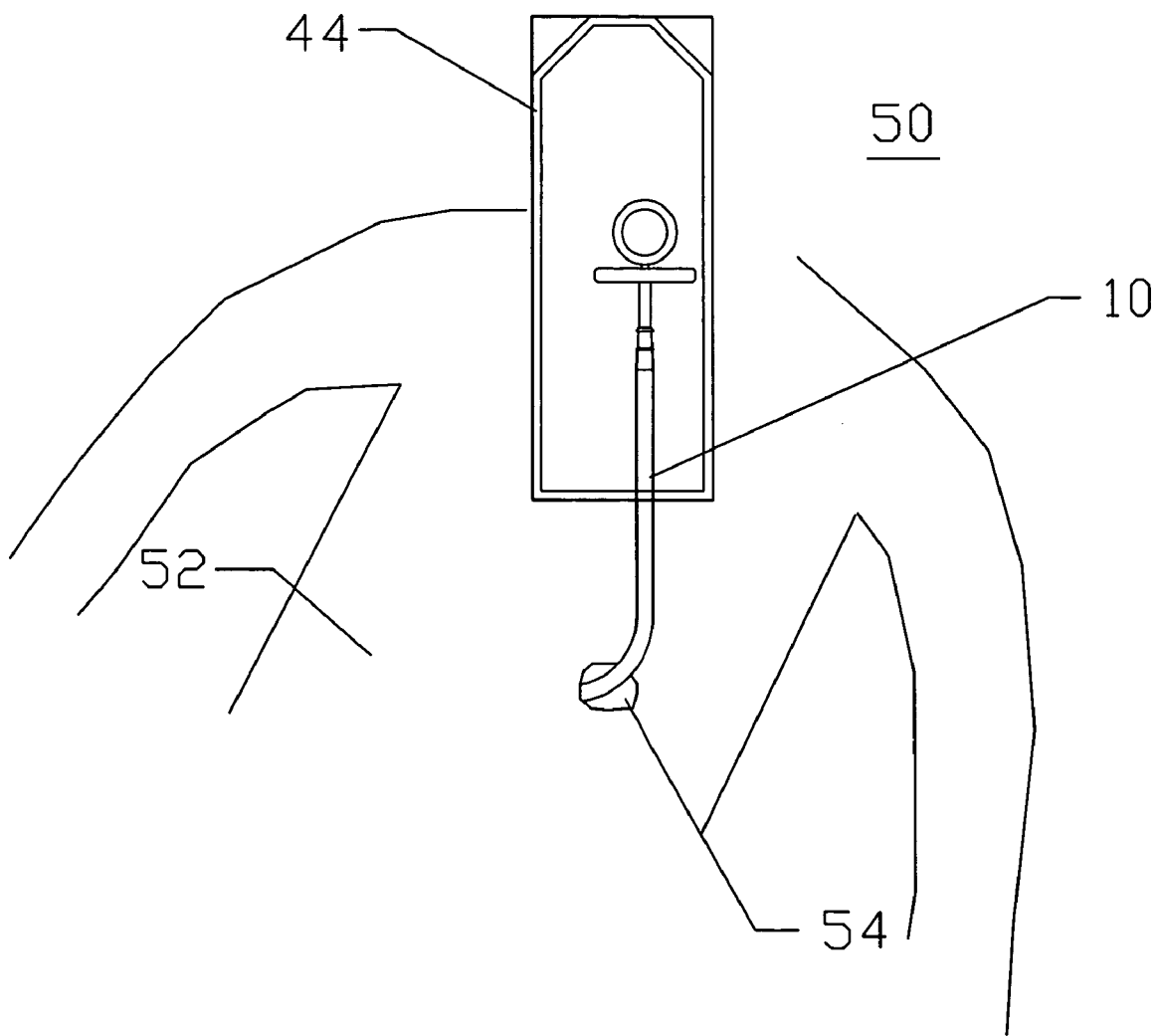
FIG. 4 illustrates the chest tube advanced into a wound in the thoracic wall of a patient or other animal.

FIG. 4 illustrates the method of installing the device 50 into a patient. The chest tube 10 is contained in a sterile inner package 44 until ready for deployment into patient 52 through an incision site 54. The access site is first prepared by swabbing or rinsing the area with betadine or other disinfectant, preferably using standard hospital or emergency procedures. The adhesive patch described below or other flexible structure further comprising a disinfectant is applied to the region of the incision. An incision is made in the chest wall using a sterile scalpel, punch or other device. A finger or, alternatively, other blunt device is next advanced through the incision to bluntly dissect through the final layers of chest wall into the chest cavity. The blunt device for dissection may optionally be comprised at the distal tip of the chest tube itself. To deploy the chest tube from its protective package, the user first opens and removes the outer sterile or aseptic packaging layer maintaining the inner package substantially intact, so that the chest tube can be placed without the need for sterile gloves to be worn by the user. Next, the user grasps the chest tube and the blunt trocar control knob through the inner layer of flexible packaging. The blunt trocar is manually retracted within the cannula exposing the sharpened distal tip of the cannula. The cannula is punched through the inner layer of package by way of the sharp tip and the blunt trocar is now replaced to its protective position. The chest tube is now advanced into the prepared incision in the chest cavity. During deployment, the inner package is left intact over the chest tube, while on the distal end of the tube extends out of the package, ensuring sterility of the chest tube to the maximum extent possible.

Figure 5A:
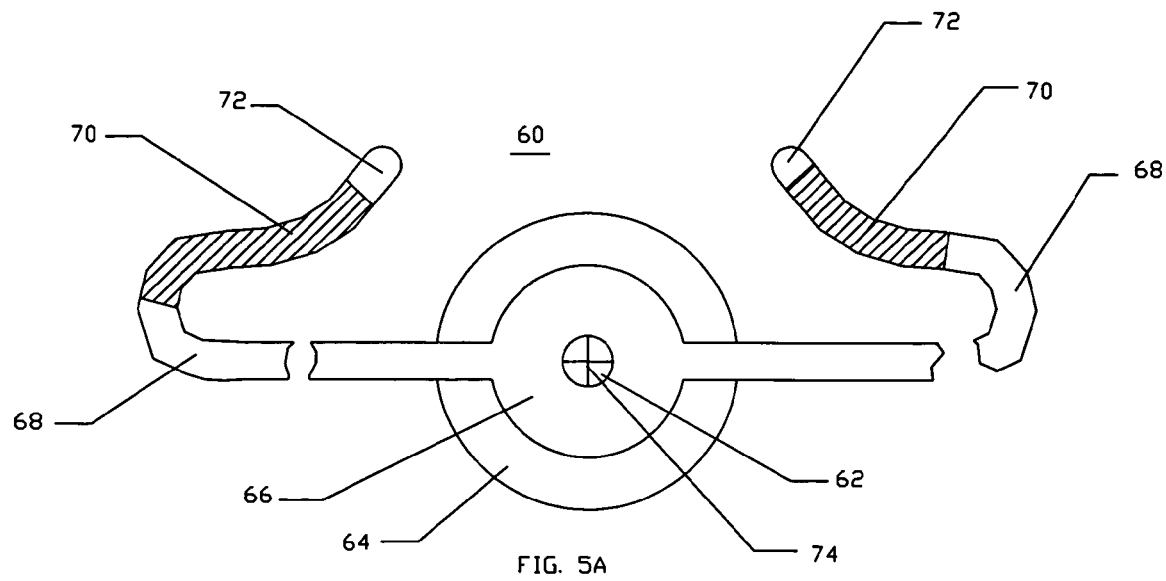
FIG. 5A illustrates a top view of a protective wound disc.

FIG. 5A illustrates an aseptic hold-down patch 60 to be used with the chest tube 10. The aseptic hold down patch 60 comprises a penetration region 62, a main adhesive region 64, a hold down plate 66, a plurality of hold down straps 68, an adhesive region 70 on each strap 68, a plurality of pull tabs 72, and a plurality of partially completed slits 74 within the penetration region 62. As illustrated, the patch 60 is a disc, but it may be provided in any suitable shape or configuration.

Referring to FIG. 5A, the main adhesive disc 64 is permanently affixed to the hold-down disc 66 with adhesive or other fasteners. The hold down-straps 68 are affixed to, or integral to, the hold-down disc 66. The adhesive region 70 is on the hold-down strap 68 and the pull-tab 72 is at the end of the hold-down strap 68. The penetration region 62 is at the center of both the main adhesive disc 64 and the hold down disc 66. The penetration region 62 comprises slits 74 that pass partially, but not completely, through from the outside. The slits 74 may also advantageously fully penetrate the main adhesive disc 64 and the hold down disc 66. The central area around the penetration region 62 is preferably transparent or clear, to permit viewing of the incision site while the hold down disc 66 and main adhesive disc 64 are being advanced against the patient. The hold down disc 66 and the backbone structure of the main adhesive disc 64 are fabricated from materials including, but not limited to, cardboard, polystyrene, polyvinyl chloride, polyester, polyimide, polyamide, polyethylene, polypropylene, and the like, and they may be integrally formed. While the hold down disc 66 and the main adhesive disc 64 should be semi-rigid or have reduced flexibility, the hold down straps 68 are preferably of greater flexibility. The flexibility can be achieved by weaving or knitting structures of the polymers such as polyester cloth and the like.

The adhesive region 70 is designed to be fastened to the chest tube 10 to hold said chest tube 10 from being dislodged from the patient. The adhesive region 70 may alternatively be fabricated using Velcro® or other fastener systems, including hook and loop-type fabric fasteners, that mate with corresponding systems attached to the chest tube 10. If adhesives are used in the adhesive region 70, a paper or plastic cover strip, removable before use, is desirable to protect the adhesive.

The main adhesive disc 64 is coated, on the patient side, with a strong skin adhesive. Such adhesives include cyanoacrylates, but preferably include aggressive adhesives, such as hydrophilic hydrogels, that may be removed or un-adhered such as those adhesives that are used on the pads of electrocardiogram (EKG) electrodes. The adhesive may optionally comprise antigenic, antibiotic or anti-microbial agents such as, but not limited to, silver azide, silver chloride, antibiotics, and the like. The adhesive region is, preferably, covered with a plastic or paper cover, that is removed by the practitioner, prior to adhering the disc to the patient. Prior to adhesion of the hold down disc 60 to the patient, the practitioner preferably scrubs the area with betadine or other antimicrobial agent using standard aseptic technique.

Figure 5B:
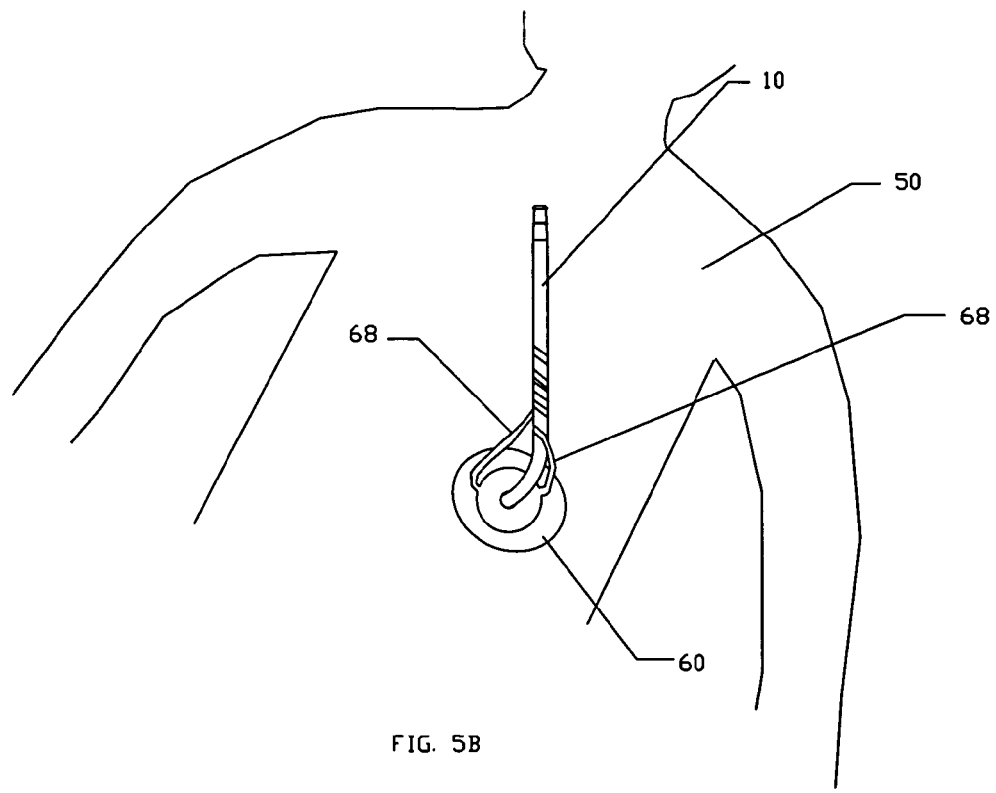
FIG. 5B illustrates a top view of the protective wound disc with its straps wrapped around and adherent to the chest tube.

FIG. 5B shows the hold-down disc 60 adhered to the patient 50. The hold down straps 68 are wrapped around and adhered to the chest tube 10, holding the chest tube 10 in place. The cutter handle 22 and obturator handle 26 are not visible in FIG. 5B because they have been removed from the chest tube 10.

FIG. 6A illustrates an incision apparatus 100, with its cutter retracted. The incision apparatus 100 comprises a cutting blade 102, a shaft 104, a chest plate 106, a bearing 108, a housing 110, a spring 112, a handle 114, a travel stop 116, a locking mechanism 118, and a lock extension 120.

Referring to FIG. 6A, the cutting blade 102 is permanently affixed to the distal end of the shaft 104 while the handle 114 is permanently affixed to the proximal end of the shaft 104. The shaft 104 slideably moves through bearing 108 that is permanently affixed to the housing 110, which is further affixed to the chest plate 106. The spring 112 biases the shaft 104 so that the cutting blade 102 is retracted within the housing 110. The travel stop 116 is affixed to the housing 110 and limits travel of the handle 114. The locking mechanism 118 is affixed to either the chest plate 106 or the housing 110. The locking mechanism 118 is affixed to the lock extension 120. The lock extension 120 selectably engages the cutter 102 to prevent inadvertent advancement of said cutter 102 until desired.

The cutting blade 102 is preferably fabricated from stainless steel and is configured to form a cross or "X". The cutting blade 102 may also be a single blade or other configuration. The cutting blade 102 may be pointed or rounded in side view.

The spring 112 is preferably a concentric coil spring fabricated from stainless steel, Elgiloy, nitinol or other suitable spring material. The spring 112 can also be a leaf spring or have a non-concentric configuration.

The chest plate 106, the housing 110, the handle 114, the locking mechanism 118, the lock extension 120, and the travel stop 116 are fabricated from polymeric materials including, but not limited to, PVC, polycarbonate, acrylic, Delrin, polypropylene, PEEK or other suitable rigid material. The chest plate 106 is preferably transparent and may be provided with an adhesive on the skin-contacting surface 107.

Referring to FIG. 6A, the chest plate 106 is placed against the chest of the patient so that the center of the chest plate 106 is at the desired incision point. The chest plate 106 is held against the chest of the patient and the locking mechanism 118 is disengaged. Manual force is applied to the handle 114, which advances the cutter 102 until such point as the handle 114 hits the travel stop 116. Release of manual pressure from the handle 114 causes the spring 112 to retract the blade 102 back within the housing. The incision apparatus is designed to cut through only the skin, fascia, and fat of the patient and limit deeper advancement of the blade 102. The travel stop 116 prevents the blade 102 from penetrating lower than the level of the ribs, so as to avoid damage to underlying organs.

FIG. 6B illustrates a side view of an incision apparatus 100 with its cutter advanced. The incision apparatus 100 comprises a cutting blade 102, a shaft 104, a chest plate 106, a bearing 108, a housing 110, a spring 112, a handle 114, a travel stop 116, a locking mechanism 118, and a lock extension 120. The locking mechanism 118 has been withdrawn permitting the cutting blade 102 to be forced beyond the face of the chest plate 106 and into the patient. The handle 114 is now impinging on the travel stop 116 to prevent the cutting blade 102 from being advanced too far beyond the chest plate 106 and thus injure the patient. The spring 112 is compressed to provide biasing of the cutting blade 102 away from the patient after the force on the handle 114 is removed.

FIG. 6C illustrates a bottom view of an incision apparatus 100, according to aspects of an embodiment of the invention. The cutting blade 102 is clearly shown with an "X" configuration in this embodiment. The shaft 104 and the bearing 108 are visible in this view.

Figure 7:
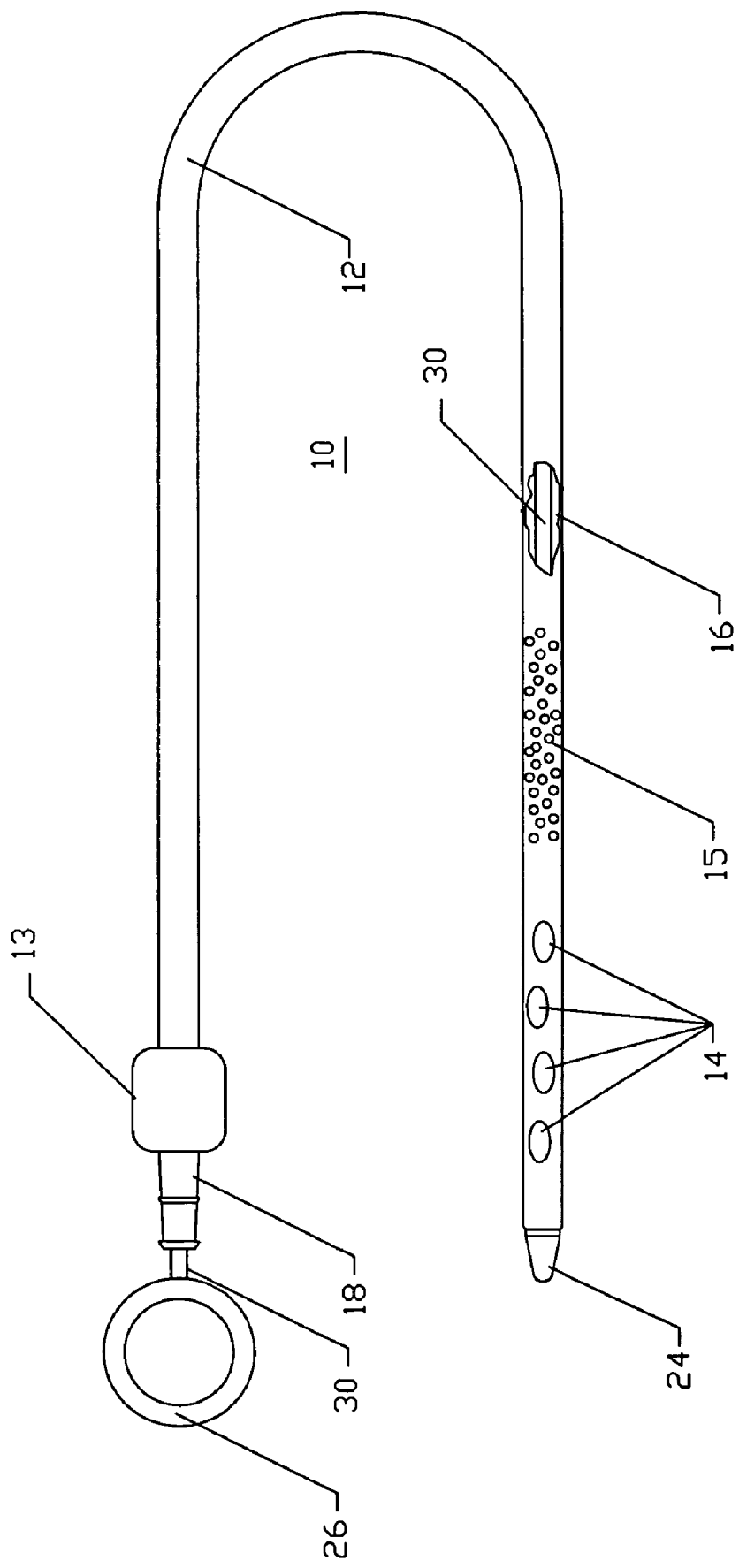
FIG. 7 illustrates a side view of a chest tube, comprising a blunt trocar suitable for penetrating the package and bluntly dissecting into the chest of the patient.

FIG. 7 illustrates another embodiment of the chest tube 10. The chest tube 10 comprises a length of tubing 12, an optional valve 13, a plurality of distal openings or drainage ports 14, an optional gripping or friction surface 15, a central lumen 16, a drainage connector 18, an obturator 24, an obturator handle 26, and an obturator control rod 30. The length of tubing 12 comprises a wall and a central lumen 16. The length of tubing 12 has a proximal and a distal end. The openings 14 are holes extending through the tubing wall from the exterior to the central lumen 16. The optional valve 13 is affixed integral to or separate from the tubing 12. The friction surface 15 is integral to the tubing 12 but may be a separate structure slidably disposed over the tubing 12. The drainage connector 18 is affixed to the proximal end of the tubing 12. The obturator 24 is slidably disposed within the central lumen 16 of the tubing 12. The obturator 24 is affixed to the distal end of the obturator control rod 30. The obturator handle 26 is affixed to the proximal end of the obturator control rod 30 and extends outside the drainage connector 18.

The obturator 24 could also be termed a nose cone, blunt trocar or other designation. The obturator 24 is wedge shaped but could alternatively be symmetrical in configuration. The obturator 24 is not sharp enough to cut through skin under pressures up to 20 pounds. The obturator 24 is, however, able to optionally bluntly dissect muscle and pleural tissue under forces approximating 20 pounds. The obturator 24 is removed from the chest tube 10 by grasping the obturator handle 26 and withdrawing said obturator handle 26, which removes the obturator 24 by withdrawing the attached obturator control rod 30. The obturator control rod 30 possesses column strength and resistance to elongation under tension but is flexible to at least some degree. This flexibility permits the obturator control rod 30 and the chest tube 10 to bend during insertion into the patient, thus minimizing the risk of internal organ perforation. The obturator control rod 30 optionally possesses variable flexibility. It is preferred that the obturator control rod 30 is more flexible toward the distal end and less flexible toward the proximal end. Referring to FIGS. 1B, 1C and 7, this embodiment of the chest tube 10 may also comprise a malleable shaft 32.

Figure 8A:
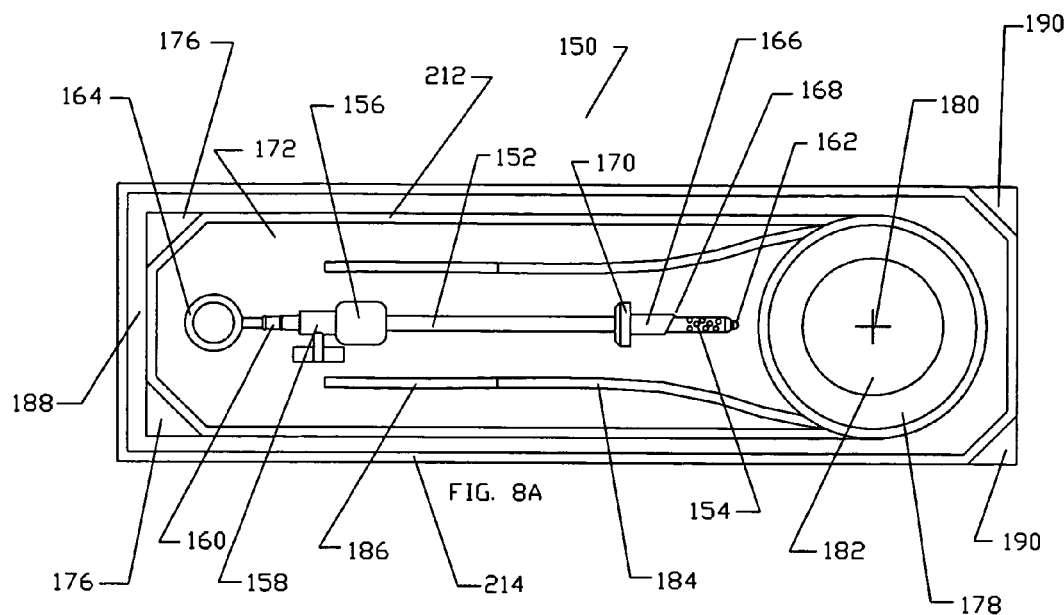
FIG. 8A illustrates a top view of a chest tube in a package comprising an integral protective wound disc and tie down straps.

FIG. 8A illustrates a packaged chest tube system 150 comprising an axially elongate cannula tube 152 with a central lumen (not shown), a plurality of distal openings 154, an optional one-way valve 156, an optional shutoff valve 158, a connector 160, an obturator further comprising a shaft 162 and a handle 164, a trocar further comprising an axially elongate cylindrical shaft 166, a beveled tip 168, a limit stop 170, an inner pouch 172 further comprising a plurality of chevron opening regions 176, a hold down disc 178 further comprising a protective cover sheet (not shown), a central slit region 180, a substrate with a clear window area 182 a plurality of hold down ties 184 each further comprising a cannula grip region 186, and a skin adherence region (not shown), and an outer pouch 188 further comprising a plurality of chevron opening areas 190, and labeling (not shown).

Referring to FIG. 8A, the cannula tube 152 is an axially elongate tube with a central through lumen having a proximal and a distal end. The distal end of the cannula tube 152 comprises a plurality of perforations, penetrations, or holes 154 that communicate between the exterior of the cannula 152 and the central lumen. The proximal end of the cannula tube 152 is permanently or removably affixed to the one-way valve 156 and further removably affixed, preferably in series, to the shutoff valve 158 as well as the connector 160. The shaft 162 of the obturator is removably, and slidably placed through the central lumen of the cannula tube 152. The obturator handle 164 is permanently affixed to the shaft 162 and projects out the proximal end of the cannula tube 152 and any attachments including the connector 160. The axially elongate shaft 166 of the trocar is concentrically, slidably, and movably placed over the cannula tube 152. The trocar shaft 166 is sharpened and preferably beveled on its distal end 168. The proximal end of the trocar shaft 166 is permanently affixed to the limit stop 170, which further comprises a central through lumen and slidably moves over the cannula tube 152.

Further referring to FIG. 8A, the outer pouch 188 is preferably comprised of an upper layer and a lower layer (not shown). The upper layer and the lower layer are preferably heat sealed together so as to form a complete barrier against microbial contaminants. The band where the upper layer is sealed to the lower layer is called the heat seal 214. The outer pouch 188 preferably comprises one or more openable areas, or chevrons 190, that are comprised by heat seals that are disposed diagonally across the corners of the outer pouch 188 to permit a user to grab the upper layer separately from the lower layer and tear the two layers apart at the chevron 190. The outer pouch 188 further preferably comprises a label, which is either integral or adhered to the outer pouch 188. The inner pouch 172 is fabricated using similar techniques as the outer pouch 188. Preferably the inner pouch 172 comprises an upper and a lower layer that are heat sealed together with opening chevrons 176 and heat seals 212. The inner pouch 172 further comprises a hold down disc 178 that is permanently affixed, removable, or integral to the distal end of the inner pouch 172. The hold down disc 178 is fabricated from a substrate 182 that forms the main body of the hold down disc 178. The substrate 182 is coated on the distal most side with an adhesive that is skin compatible and preferably adheres to wet skin. The substrate 182 further comprises a window area, which is a clear or transparent region permitting visibility through the hold-down disc at least in its central region. The substrate 182 is partially, or completely perforated at its central region in, for example, a cross or "X" shape, to permit easy penetration of the hold-down disc by the distal tip of the cannula 152. The hold-down disc 178 is preferably folded flat so as to be insertable into the outer pouch 188 with a minimum profile.

The hold-down disc 178 further is permanently affixed to one or more tie down straps 184 that further are coated with adhesive near the ends to form adhesive regions 186. The tie-down straps 184 are disposed within the interior of the inner pouch 172. They may be separate or pre-attached to the cannula 152. If separate, the adhesive regions 186 of the tie down straps 184 are covered by a protective peel-away layer (not shown).

The hold-down disc 178, in another embodiment, is a flexible, elastomeric, rigid or semi-rigid piece of polymer, metal, or the like and is configured with a soft, pliable exterior edge. The hold-down disc 178, in this embodiment, is a suction cup that adheres to the patient's skin by way of suction. A port, valve, and suction bulb for manual evacuation are optionally beneficial to this embodiment in that they can be used to enhance the vacuum bond created by the basic suction cup design.

The hold down disc 178 is, preferably, affixed to or integral to the inner pouch 172 and the proximal side of the hold down disc 178 comprises part of the interior of the inner pouch 172. Because the inner pouch 178 is flexible, the hold-down disc 178, which is normally in the plane orthogonal to that of the inner pouch 172 or the cannula 152, may be turned sideways so that it resides in a generally coplanar disposition relative to the inner pouch 178 and cannula 152 during packaging, shipping, and storage.

The trocar comprised by the shaft 166, the limit stop 170, and the sharpened end 168 is very short. The trocar is intended to be forced into a skin incision made in the patient's chest. The trocar cannot penetrate very far because the distance between the sharpened end 168 and the distal end of the limit stop 170 is limited. In a preferred embodiment, the limit stop 170 is large in diameter and stops against the outside of the skin. The diameter of the limit stop 170 is between 1 and 20 cm, and preferably between 2 and 10 cm and more preferably between 3 and 6 cm. The length of the shaft 166 is between 1 and 10 cm and preferably between 2 and 5 cm. The length of the shaft 166, in this embodiment, will need to be tailored to the individual because each person has a different amount of fat so different sizes may be required, for example, large, medium, and small. Thus, the distal segment of the cannula, which enters the body may be provided in various pre-determined lengths to suit patients of varying physique, and the practitioner may select a suitably short device for use after appraisal of the patient. In another embodiment, the distal segment can be made to telescope or extend to continuously variable or pre-determined set lengths to fit persons of various skin and fat thicknesses. A lock is used to maintain the length once set by the user.

In another embodiment of the trocar, the limit stop is smaller in diameter and stops against the outside of the ribs. In this latter embodiment, the limit stop 170 is passed inside a skin incision and through fat layers so that it stops at or near the outer region of the ribs. The diameter of the limit stop 170 in the latter embodiment is between 1 and 5 cm and preferably between 1 and 3 cm. The length of the shaft 166 is between 1 and 5 cm and, preferably between 1.4 and 4 cm so that it passes through the ribs and into the pleural space but does not project far into the pleural space. This embodiment avoids much of the issues with regard to amount of body fat on a person and allows for a one-size-fits-all approach, so that the distal segment of the cannula may be provide din a single, predetermined length suitable for safe, stop-limited penetration through the rib cage.

Figure 8B:
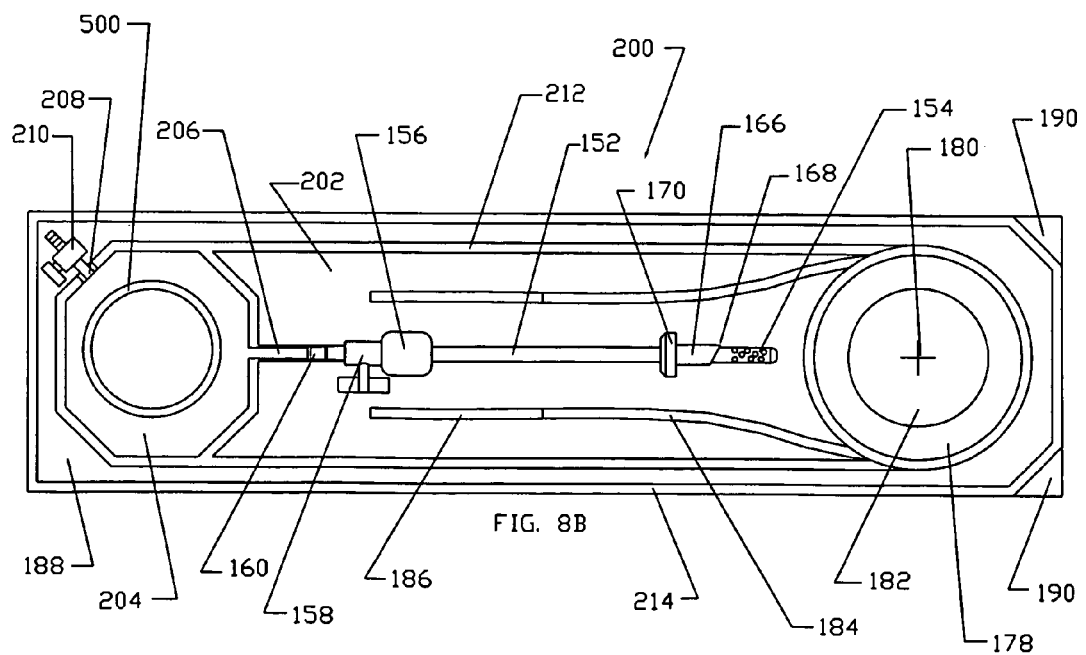
FIG. 8B illustrates a top view of a chest tube in a package comprising an integral protective wound disc and tie down straps along with an integral pleural drainage system.

FIG. 8B illustrates a packaged chest tube system 200 comprising an axially elongate cannula 152 with a central lumen (not shown), a plurality of distal openings 154, an optional one-way valve 156, an optional shutoff valve 158, a connector 160, a trocar further comprising an axially elongate cylindrical shaft 166, a beveled tip 168, and a limit stop 170, an inner pouch 202 further comprising an upper layer and a lower layer (not shown), a plurality of heat seals 212, a drainage volume 204, a drainage inlet manifold 206, an optional vacuum port 208, an optional stopcock 210, an optional vacuum pump (not shown), a hold down disc 178 further comprising a protective cover sheet (not shown), a central slit region 180, a plurality of hold down ties 184, a substrate with a clear window area 182, and a skin adherence region (not shown), and an outer pouch 188, further comprising an upper layer and a lower layer (not shown), a plurality of heat seals 214, a plurality of chevron opening areas 190, and labeling (not shown). Also shown is an optional internal spring 500 configured to expand the drainage volume 204, following selective and controlled unlocking, unlatching, or release of the spring 500.

The embodiment of FIG. 8B is similar to that of FIG. 8A, except that the inner pouch 202 comprises the drainage volume 204, the drainage inlet manifold 206, the optional vacuum port 208, the optional stopcock 210, and the optional vacuum pump. These components are either integral to the inner pouch 202 or are affixed and bonded to the inner pouch 202 using heat, solvents, adhesives, ultrasonic welding, or the like. Referring to FIG. 8A, the cannula 152 of FIG. 8B does not comprise an obturator shaft 162 or handle 164, although these could be added, if desired. In this embodiment, the extreme distal tip of the cannula 152 is advantageously of increased stiffness, or has decreased flexibility, relative to the rest of the shaft 152. In this way, by careful location of the distal tip of the cannula 152 relative to the trocar shaft 166 and sharpened end 168, the cannula 152 serves the function of the blunt obturator.

Referring to FIG. 8B, the drainage volume 204 serves as an integral collection device, much like a pleur-evac. The drainage volume 204 is connected to the connector 160 of the cannula 152 by way of the drainage manifold 206. The drainage volume may comprise an optional standoff to maintain a finite internal volume for maintenance of a pre-applied or generally applied vacuum. The vacuum pump may be a simple manual bulb or it may be any of the typical electromechanical devices available.

Further referring to FIGS. 8A and 8B, the method allows for placement of a chest cannula 152 in a patient without the need to use gloves since the cannula 152 and any associated apparatus is handled through the protective pouches or bags. The entire system is sterilized. The chest tube 152 and its components, and the inner pouch 202, both inside and outside, are maintained sterile by the outer pouch 188. The patient incision site is first swabbed with iodine, betadine, or other disinfectant. An incision is made, with a sharp blade, through the skin and into the fat layers. After removal of the outer pouch 188, the chest tube or cannula 152 may be manipulated through the inner pouch 202. The hold down disc 178 is adhered to the skin at the incision site. The trocar and concentrically mounted chest tube 152 are forced through the central slits 180 in the hold-down disc 178 and into the incision. The trocar is forced into the incision until the limit stop 170 hits the hold down disc 178. The trocar is withdrawn and the chest tube cannula 152 is advanced into the incision. Once placement is acceptable, the tie down straps 186 are wrapped around the cannula shaft 152 and chest drainage management can commence.

FIG. 9A illustrates an expandable trocar 250 comprising a limit stop 252, a plurality of split sleeves 254, an obturator stop 256, an obturator handle 258, and an obturator shaft 260.

Referring to FIG. 9A, the plurality of split sleeves 254 are disposed concentrically at their minimum potential diameter. The split sleeves 254 are embedded in or affixed to elastomeric or malleable material that is affixed to a central lumen of the limit stop 252. The obturator shaft 260 is preferably rounded at its distal end and is affixed to the obturator stop 256, which is further affixed to the obturator handle 258. The obturator shaft 260 is movably, removably, and slidably disposed within the central lumen described by the split sleeves 254. The rounded distal end of the obturator shaft 260 is positioned so that when the obturator stop 256 is against the proximal side of the limit stop 252, the rounded section fully projects beyond the distal end of the split sleeves 254.

The number of split sleeves 254 is between 2 and 100, and preferably between 4 and 50, and more preferably between 6 and 20.

The region between the split sleeves 254 is either open or it is filled in with an elastomeric material such as, but not limited to polyurethane, silicone elastomer, thermoplastic elastomer, latex rubber, polyethylene foam, polyvinyl chloride foam, polyurethane foam, and the like. In another embodiment, the split sleeves 254 are covered by an elastomeric layer fabricated from the same materials as that used for the fill described above.

FIG. 9B illustrates a bottom view of the expandable trocar shown in FIG. 9A, further comprising the obturator shaft 260, the plurality of split sleeves 254, the limit stop 252, and the expandable region 262.

Referring to FIGS. 9A and 9B, the limit stop 252 as well as all components of the obturator are preferably fabricated from metals such as, but not limited to, stainless steel, cobalt nickel alloys, nitinol, or titanium, or polymeric materials such as, but not limited to, polyethylene, polypropylene, polycarbonate, polyester, polyvinyl chloride, polyamide, ABS, and the like. The elastomeric or malleable material, in which the split sleeves 254 are embedded, is preferably a material such as, but not limited to polyurethane, silicone elastomer, thermoplastic elastomer, latex rubber, polyethylene foam, polyvinyl chloride foam, polyurethane foam, and the like. The split sleeves 254 are fabricated from materials such as, but not limited to, stainless steel, cobalt nickel alloys, nitinol, titanium, polyethylene, polycarbonate, polypropylene, polyester, polyvinyl chloride, polyamide, ABS, PTFE, FEP, and the like. The elastomeric region in the limit stop 252 embeds the split sleeves 254 and allows them to expand under the force of a tapered obturator or central insertable mass. In another embodiment, the elastomeric region 262 is replaced by cantilevered split sleeves 254 that are embedded into the limit stop 252. The split sleeves 254 are leaf springs and expand in the presence of a large insertable central mass.

FIG. 9C illustrates the expandable trocar 250 of FIG. 9A with the obturator components 260, 256, and 258 removed and a large expanding obturator 270 being inserted. The large expanding obturator 270 further comprises a tapered region 272, a blunt rounded tip (not shown), a straight shaft 274, and an expanding obturator handle 276. The expanding obturator 270 has not been inserted far enough to cause any expansion of the split sleeves 254.

FIG. 9D illustrates the expandable trocar 250 with the large expanding obturator 270 having been fully inserted therein. The split sleeves 254 have opened up forming a series of fingers that are intended to pry open or expand tissue. The blunt tip 278 of the expanding obturator 270 is visible in this view. It is preferable that the blunt tip 278 not project beyond the distal ends of the split sleeves 254 but a small amount of projection, as shown, is acceptable.

FIG. 9E illustrates a bottom view of the expandable trocar 250 with the large expanding obturator 270 having been fully inserted therein. The elastomeric or malleable region 262 has become much narrower than in the unexpanded state of FIG. 9B, due to the expansion of the embedded split sleeves 254.

Referring to FIGS. 9A through 9E, the expandable trocar permits placement of a small diameter trocar through the thoracic wall, a procedure which is fairly commonplace and easy. However, by removal of the small obturator and full insertion of the large expanding obturator 270, the trocar 250 and the hole in the tissue it supports is expanded greatly and in such a way that a chest tube could be inserted therethrough. In yet another embodiment of the expandable trocar 250, the obturator shaft 260 is sharpened and capable of cutting through the skin, fat, fascia, and muscle of the patient. The sharp tip on the obturator shaft 260, in this embodiment would be retracted automatically by standoffs that projected distally of the limit stop 252 and were attached to the obturator stop 256 or obturator handle 258. Automatic retraction of the sharp tip of the obturator shaft 260 would permit a one-step procedure or method to punch a hole in the thoracic wall and insert the trocar 250 through the ribs to the limit stop 252 without the need of a scalpel or other sharp object to make the initial skin incision. In another embodiment, the expandable trocar 250 can be made hollow with a central lumen to permit flow therethrough. The distal tip of the expandable trocar 250 can be tapered and open at the center or it can comprise fenestrations. The proximal end of the trocar can be affixed to drainage systems and valves for the purpose of chest drainage and prevention of pneumothorax.

FIG. 10A illustrates a short chest tube 300 comprising a cannula tube 302, a plurality of drainage holes 314, a limit stop 304, a tube standoff 306, a one-way valve 308, a stopcock 310, and a drainage connector 312. The short chest tube 300 is shown inserted through an incision through a skin 320, a fat layer 322, a layer of fascia 330, a region of intercostal muscle 324, between the ribs 326, through the pleura 328, and into the pleural space 332.

Referring to FIG. 10A, the cannula tube 302 is an axially elongate hollow tube with a proximal and a distal end. The proximal end of the cannula tube 302 is affixed to the limit stop 304, which is affixed to the tube standoff 306, which is affixed to the one-way valve 308, which is affixed to the stopcock 310, which is affixed to the distal end of the drainage connector 312. A central through lumen is maintained from the distal end of the cannula tube 302 to the proximal end of the drainage connector 312 so that fluid can be drained from the thoracic cavity. The one-way valve 308 prevents backflow into the thoracic cavity but opens to provide a through lumen for drainage. The stopcock 310 provides manual shutoff or opening of the through lumen. The drainage holes 314 communicate between the through lumen and the outside of the cannula tube 302. The plurality of drainage holes 314 are provided since a single hole, at the distal tip for example, might become occluded with tissue and drainage could not occur. The plurality of holes 314 separated by the material of the cannula tube 302 provides a standoff for the tissue and maximizes the surface area for drainage of the pleural space.

Referring to FIG. 10A, the short chest tube 300 may be forced between the ribs 326 and into the pleural space 332 with reduced risk of damage to internal organs since the distal end of the cannula tube 302 is rounded and blunt. In addition, the length of the cannula tube 302 is maintained short so that it projects just a small amount into the pleural space 332. The cannula tube 302 is provided, for example in several lengths to accommodate people with different thicknesses of body fat. The diameter of the cannula tube 302 is between 0.25 cm and 4 cm and preferably between 0.5 cm and 2 cm. The limit stop 304 prohibits the short chest tube 300 from being advanced too far into the patient and, thus, minimizes the risk of damage to the underlying organs such as the heart and lungs. The lengths and diameters of the limit stop 304 and the construction materials are the same as that described for the trocar 250 shown in FIGS. 9A through 9E.

FIG. 10B illustrates a short deflecting trocar and chest tube system 350 where the trocar comprises a trocar tube 352, a deflecting tip 354, a limit stop 356, and a sealing handle 358. The chest tube comprises a cannula 360, a plurality of drainage holes 362, an optional obturator shaft 364 and an optional obturator handle 366, a one-way valve 368, a stopcock 370, and a drainage connector 372. The short deflecting trocar and chest tube system 350 is shown inserted through an incision through a skin 320, a fat layer 322, a layer of fascia 330, a region of intercostal muscle 324, between the ribs 326, through the pleura 328, and into the pleural space 332.

Referring to FIG. 10B, the short deflecting trocar and chest tube system 350 permits placement of a short trocar through the ribs and into the pleural space. A chest tube cannula 360 is then inserted therethrough and deflected so that it can route parallel to the plane of the chest wall to a desired location. The obturator shaft 364 and the obturator handle 366 are preferably omitted from the system but may advantageously be added if additional column strength or steerability is desired.

The trocar sealing handle 358 is fabricated from rigid polymers such as, but not limited to ABS, pvc, polyethylene, polypropylene, polysulfone, polycarbonate, and the like, and further comprises a central lumen with an elastomeric seal through which the cannula shaft 360 may slidably and movably pass but which seals and prevents the passage of air or liquid around said cannula shaft 360. The elastomeric seal (not shown) is fabricated from materials such as, but not limited to, silicone elastomer, latex rubber, thermoplastic elastomer, polyurethane, and various closed-cell or open-cell foams. The inner surface of the elastomeric seal is advantageously coated with a lubricant such as silicone oil, hydrogel, or the like, to facilitate movement of the cannula shaft 360 through the sealing handle 358.

Referring to FIG. 10C, the limit stop 304 is sized and dimensioned to permit advancement through the fat layer 322 overlying the patient's rib cage, but prevent advancement into the narrow space between the ribs 326. In this arrangement, the length of the tube 302 distal to the stop is set at a predetermined length corresponding to the average thickness of the ribs, so that the distal tip of the tube extends into the pleural space 332 without significant risk of injuring tissue therein. The chest tube may be similar to the chest tubes of the previous figures, except the flange stops at the outside aspect of the ribs.

FIG. 11A illustrates a side view of an inner package for a chest tube 10 comprising an integral drainage volume 204 bounded by a flexible wall 504 and volume expansion spring 500 in its collapsed, stored configuration. The chest tube package further comprises a clip 502 to maintain the volume expansion spring 500 in its collapsed position. The flexible wall 504 is the same as the material of the inner pouch 202. The extent of the volume 204 is limited by the heat seals 212 (FIG. 8A) on the inner pouch 202 of FIG. 8B. The spring 500 can be a coil spring, a leaf spring, or other structure that opens elastomerically. The spring 500 can be fabricated from materials such as, but not limited to, stainless steel, spring steel, titanium, nitinol, polymers such as polycarbonate, and the like. The drainage volume 204 is integral to the inner pouch 202 of FIG. 8B. The clip 502 can be external, as shown, or it can be internal. It can be a clip that is manipulated through the inner pouch 202 and released from the spring 500 to allow the spring 500 to open. The clip 502 can also be a simple ratchet that is released when the spring 500 is first squeezed together.

FIG. 11B illustrates a side view of the chest tube package of FIG. 11A which is expanded and exerting a vacuum on the drain line leading from the chest tube 10. The clip 502 from FIG. 11A has been removed allowing the volume expansion spring 500 to expand to its naturally open biased position, thus opening the space between the flexible walls 504 and increasing the size of the drainage volume 204. When the volume 204 is increased, it creates a vacuum within the volume 204, which allows for assisted drainage of fluids through the chest tube 10. The volume 204 can range between 10-cc and 1,000-cc and preferably between 50-cc and 500-cc. The entire system is disposable, following use.

The advantage of the aforementioned devices and methods improves the ease, and convenience, with which a chest tube may be placed, especially by less well-trained personnel such as paramedics and emergency medical technicians. Such circumstances, where the device is especially useful, is in the field on patients experiencing a trauma pneumothorax, sucking chest wound, or the like.

Application of the chest tube system provides improved speed of application of said chest tube, especially in contaminated environments. The application of this chest tube system facilitates damage control procedures wherein the patient can be allowed to stabilize prior to definitive repair of the injuries. The aseptic hold-down disc and the incision apparatus allow for quicker application of said chest tube by paramedics and emergency personnel with less chance of wound contamination, internal damage to the patient or chest tube dislodgement. Such damage control procedures have been shown to improve patient outcomes and save lives.

The present invention may be embodied in other specific forms without departing from its spirit or essential characteristics. For example, the aseptic hold down disk may have more than two straps to restrain the chest tube. The incision apparatus may have a cocking mechanism to retract and then fire the cutter, rather than using positive hand pressure to advance the cutter. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

What is claimed is:

1. An apparatus adapted for chest drainage comprising:
   a tube characterized by a proximal end, a distal segment adapted fro insertion into the chest and a lumen communicating from the proximal end to the distal end;
   a plurality of perforations at the distal end of said tube communicating between the lumen and the outside of the tube;

a connector at the proximal end of said tube for connecting the through lumen of said tube to drainage apparatus;

a cutter located at the distal end of said tube;

an obturator or blunt tip capable of selectively protecting the sharp edge of said cutter; and means for longitudinally translating the obturator relative to the cutter such that the obturator may be selectively advanced to a position distal to the cutter.

2. The apparatus of claim 1 wherein said obturator is retractable into the lumen of said tube.

3. The apparatus of claim 1 wherein said obturator is removable from the lumen of said tube.

4. The apparatus of claim 1 wherein said obturator or blunt tip is automatically advanced following penetration of the chest.

5. The apparatus of claim 1 wherein said tube is packaged inside a sterile barrier that may be pierced with said cutter.

6. The apparatus of claim 1 wherein said obturator is operably connected to a handle located near the proximal end of said tube.

7. The apparatus of claim 1 wherein said tube further comprises a malleable element disposed along at least a part of the length of said tube.

8. The apparatus of claim 1 wherein said tube further comprises a flange to limit penetration depth of the tube when the tube is inserted into an incision.

9. A method of achieving chest drainage at an incision site on a patient, said method comprising the steps of:

providing a protective patch having one or more straps extending therefrom, adhering a protective disc with its center over the incision site; making an incision or a hole partially through the thickness of the chest wall at the incision site;

thereafter bluntly dissecting through the remainder of the thickness of the chest wall at the incision site;

providing a chest tube that is sealed within a sterile barrier package, said chest tube characterized by a proximal end, a distal segment adapted for insertion into the chest, and a lumen communicating from the proximal end to the distal segment;

puncturing a sterile package containing said chest tube;

advancing said chest tube out of said packaging;

inserting said chest tube into the prepared incision in the patient's chest;

attaching said chest tube to straps attached to the protective disc to hold the chest tube in place; and enabling drainage of liquid through the chest tube from the patient's chest cavity.

10. The method of claim 9 wherein the drainage is enabled by expanding a volume operably connected to the proximal end of the lumen of the chest tube so as to generate a vacuum within the lumen.

11. The method of claim 9 wherein the initial incision in the chest wall is made with a punch.

12. The method of claim 9 wherein the drainage is enabled by allowing a spring to expand a volume operably connected to the proximal end of the lumen of the chest tube.

13. An apparatus adapted for chest drainage comprising:

an axially elongate tube further comprising a proximal end, a distal end and a through lumen;

a plurality of perforations at the distal end of said tube communicating between the through lumen and the outside of the tube;

a connector at the proximal end of said tube for connecting the through lumen of said tube to drainage apparatus;

a flange affixed to the tube, wherein the flange limits the depth of penetration of the tube within a patient; and a removable obturator or blunt tip, coaxially mounted to the distal end of said tube, wherein said removable obturator or blunt tip is able to bluntly dissect tissue.

14. The apparatus of claim 13 wherein said flange is configured to stop at the outside surface of the skin.

15. The apparatus of claim 13 wherein said flange is configured to stop at the outside aspect of the ribs.

16. The apparatus of claim 13 further comprising a deflector, wherein said deflector is capable of diverting a secondary catheter laterally, when said secondary catheter is passed through said apparatus.

17. The apparatus of claim 16 further comprising a seal between the apparatus and the secondary catheter.

18. The apparatus of claim 13 wherein said apparatus is short, rigid and blunt, and wherein said apparatus cannot be inserted into a patient's chest wall so as to cause damage to internal organs.

19. The apparatus of claim 13 further comprising a patch, wherein the adhesive patch can be affixed to the patient's chest wall around the apparatus.

20. The apparatus of claim 13 wherein the obturator or blunt tip is not removable.

* * * * *